US007655771B1

(12) United States Patent
Wojnowski et al.

(10) Patent No.: US 7,655,771 B1
(45) Date of Patent: Feb. 2, 2010

(54) POLYMORPHISMS IN THE HUMAN CYP3A4 AND CYP3A7 GENES AND THEIR USE IN DIAGNOSTIC AND THERAPEUTIC APPLICATIONS

(75) Inventors: Leszek Wojnowski, München (DE); Regina Eiselt, Eurasburg (DE)

(73) Assignee: PGx Health, LLC, Newton, MA (US)

( * ) Notice: Subject to any disclaimer, the term of this patent is extended or adjusted under 35 U.S.C. 154(b) by 353 days.

(21) Appl. No.: 10/070,587

(22) PCT Filed: Sep. 1, 2000

(86) PCT No.: PCT/EP00/08570

§ 371 (c)(1),
(2), (4) Date: Jul. 10, 2002

(87) PCT Pub. No.: WO01/20025

PCT Pub. Date: Mar. 22, 2001

(30) Foreign Application Priority Data

Sep. 10, 1999 (EP) .................................. 99118120

(51) Int. Cl.
*C07H 21/02* (2006.01)
(52) U.S. Cl. ..................................... 536/23.1
(58) Field of Classification Search ................ 536/23.1, 536/24.3, 24.31, 24.33
See application file for complete search history.

(56) References Cited

U.S. PATENT DOCUMENTS 6,025,131 A * 2/2000 Larossa et al. .................. 435/6
6,821,724 B1 * 11/2004 Mittman et al. ................ 435/6

FOREIGN PATENT DOCUMENTS

| EP | 0 759 476 | 2/1997 |
| WO | WO 91/10745 | 7/1991 |
| WO | WO 99/13106 | 3/1999 |
| WO | WO 00/24926 | 5/2000 |

OTHER PUBLICATIONS

Westlind et al. (IDS, 1999).*
Lichter (IDS, 1999).*
Overbeek (1994, "Factors affecting transgenic animal production," Transgenic animal technology, pp. 96-98).*
Wall, 1996 Theriogenology, vol. 45, pp. 57-68.*
Houdebine, 1994, J. Biotech. vol. 34, pp. 269-287.*
Kappell, 1992, Current Opinions in Biotechnology, vol. 3, pp. 548-553.*
Cameron, 1997, Molec. Biol. 7, pp. 253-265.*
Niemann, 1997, Transg. Res. 7, pp. 73-75.*
Mullins (1993, Hypertension, vol. 22, pp. 630-633).*
Mullins (1990, Nature, vol. 344, 541-544).*
Hammer (1990, Cell, vol. 63, 1099-1112).*
Mullins, 1989, EMBO J., vol. 8, pp. 4065-4072.*
Taurog, 1988, Jour. Immunol., vol. 141, pp. 4020-4023.*
Mullins (1996, J. Clin. Invest. vol. 98, pp. S37-S40).*
Gura (Science, v278, 1997, pp. 1041-1042).*
Freshney (Culture of Animal Cells, A Manual of Basic Technique, Alan R. Liss, Inc., 1983, New York, p. 4).*
Dermer (Bio/Technology, 1994, 12:320).*
Verma et al. (1997) Nature vol. 389, p. 239-242.*
Marshall (1995) Science, vol. 269, Issue 5227, pp. 1050-1055.*
Eck et al. (Goodman & Gilman's The Pharmacological Basis of Therapeutics (1996), 9th Edition, Chapter 5, McGraw-Hill, NY).*
Juengst (British Medical Journal (2003) vol. 326, pp. 1410-1411).*
Rubanyi (Mol. Aspects Med. (2001) 22:113-142).*
Hashimoto, H. et al., "Gene Structure of CYP3A4, an Adult-specific Form of Cytochrom P 450 in Human Livers, and its Transcriptional Control," *European Journal of Biochemistry* 218:585-595 (1993).
Sata, F. et al., "CYP3A4 Allelic Variants with Amino Acid Substitutions in Exons 7 and 12: Evidence for an Allelic Variant with Altered Catalytic Activity," *Clinical Pharmacology & Therapeutics* 67:48-56 (2000).
Westlind, A. et al., "Interindividual Differences in Hepatic Expression of CYP3A4: Relationship to Genetic Polymorphism in the 5'-Upstream Regulatory Region," *Biochemical and Biophysical Research Communications* 259:201-205 (1999).
Gellner, K. et al., "Genomic Organization of the Human CYP3A Locus: Identification of a New, Inducible CYP3A Gene Expressed in the Liver, Testes and Prostate," (Abstract) NCBI Protein and Nucleotide Databases, Nov. 15, 2000, AC=AAG32290. Cytochrome P450 Polypeptide 4; CYP3A4. Homo sapiens (Human).
Beaune et al., "Isolation and sequence determination of a cDNA clone related to human cytochrome P-450 nifedipine oxidase", *Proceedings of the National Academy of Sciences of the United States of America*, 83:8064-8068 (1986).

(Continued)

*Primary Examiner*—Brandon J Fetterolf

(57) ABSTRACT

Described are general means and methods of diagnosing and treating the phenotypic spectrum as well as the overlapping clinical characteristics with several forms of inherited abnormal expression and/or function of the CYP3A4 and CYP3A7 genes. In particular, polynucleotides of molecular variant CYP3A4 and CYP3A7 genes which, for example, are associated with insufficient metabolization and/or sensitivity of drugs, and vectors comprising such polynucleotides are provided. Furthermore, host cells comprising such polynucleotides or vectors and their use for the production of variant CYP3A4 and CYP3A7 proteins are described. In addition, variant CYP3A4 and CYP3A7 proteins and antibodies specifically recognizing such proteins as well as transgenic non-human animals comprising the above-described polynucleotide or vectors are provided. Described are also methods for identifying and obtaining inhibitors for therapy of disorders related to the malfunction of the CYP3A4 and CYP3A7 genes as well as methods of diagnosing the status of such disorders. Pharmaceutical and diagnostic compositions comprising the above-described polynucleotides, vectors, proteins, antibodies and inhibitors by the above-described method are provided. Said compositions are particularly useful for diagnosing and treating various diseases with drugs that are substrates, inhibitors or modulators of the CYP3A4 or CYP3A7 gene product.

10 Claims, 9 Drawing Sheets

OTHER PUBLICATIONS

Eiselt et al., "Identification and functional characterization of eight CYP3A4 protein variants", *Pharmacogenetics*, 11:447-458 (2001).

Hashimoto et al., "Gene structure of CYP3A4, an adult-specific form of cytochrome P450 in human livers, and its transcriptional control", *European journal of biochemistry / FEBS*, 218:585-595 (1993).

Wang et al., "Inhibitory anti-CYP3A4 peptide antibody: mapping of inhibitory epitope and specificity toward other CYP3A isoforms", *Drug Metabolism and Disposition*, 27(2):167-172 (1999).

Westlind et al., "Interindividual Differences in Hepatic Expression of CYP3A4: Relationship to Genetic Polymorphism in the 5'-Upstream Regulatory Region", *Biochemical and Biophysical Research Communications*, 259:201-205 (1999).

EMBL-Bank Accession No. A1638117, "ts50e10.x1 NCI_CGAP_Utl Homo sapiens cDNA clone Image:2232042 3' similar to gb:J04182 Lysosome-Associated Membrane Glycoprotein 1 Precursor (Human);, mRNA sequence.".

\* cited by examiner

CYP3A4 polymorphisms
Exon 3 (G6004A; Gly56Asp)
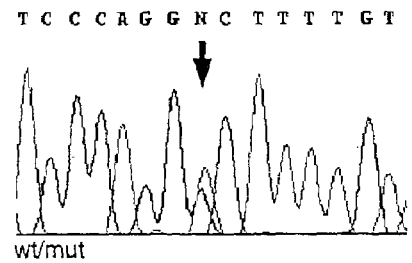
wt/mut
Oligonucleotide 3A450F (forwards)
SEQ ID NO:52    (SEQ ID NO:53*)
Intron 7 (T→G)
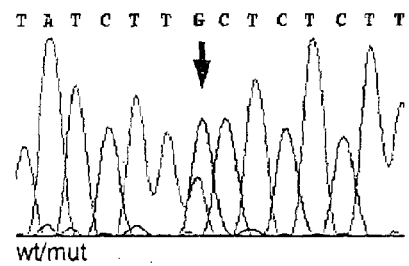
wt/mut
Oligonucleotide 3A433F (forwards)
SEQ ID NO:58    (SEQ ID NO:59*)
A CYP3A7 exon 11 polymorphism (C1229G; Thr409Arg)
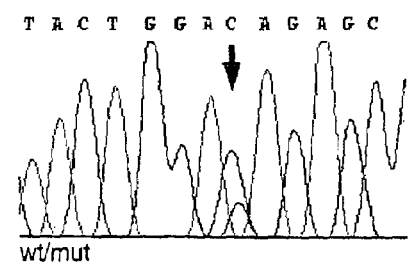
wt/mut
Oligonucleotide 3A742F (forwards)
SEQ ID NO:124
Fig. 4

SEQ ID NO:128

CYP3A4
Exon 3 (g.6004G>A, G56D)
CCTCTAACTGCCAGCAAGTCTGATTTCATTGGCTTCGACTGTTTTCAT→CCCCAATTAGAGGCAG
GGTTAAGTACATTAAAAATAATAATCAAATATTATTTTGTTTCTCCTCCCAGGG→ACTTTTGTATGT
TTGACATGGAATGTCATAAAAAGTATGGAAAAGTGTGGGGGTGAGTATTCTGGAAACTTCCATT
GGATAGACTTGTTTCTATGATGAGTTTACCCCACTGCACAGAGGACAGTCTCAGCCC

Exon 4 (Primer 3A4-52F and 3A4-37R)  SEQ ID NO:130
AGTCTGGCTTCCTGGGTTGGGCTCCAGCTGTAGAATAAGGCTGTTGATGTTTAA
TCAACTCTGTTTTTTTCACACAGCTTTTATGATGGTCAACAGCCTGTGCTGGCTA
TCACAGATCCTGACATGATCAAAACAGTGCTAGTGAAAGAATGTTATTCTGTCT
TCACAAACCGGAGGGTAAGCATTCATGTGTTGAAATTAAAATACTGATTGATTAA
ATTTATATTTTGAAATTCTTATATATTCATAGACAGTTGCCTAAAAAATGTCCAGG
AAGGTTCCACGTCCACTTC

SEQ ID NO:132

Exon 5
CTACAACCATGGAGACCTCCACAACTGATGTAGGACAAAATGTTTCTGCTTTGAA
CTCTAGCCTTTTGGTCCAGTGGGATTTATGAAAAGTGCCATCTCTATAGCTGAG
GATGAAGAATGGAAGAGATTACGATCATTGCTGTCTCCAACCTTCACCAGTGG
AAAACTCAAGGAGGTATGAAAATAACATGAGTTTTAATAAGAAACTTAAAGAATG
AATCTGGTGGGGACAGGTA

SEQ ID NO:134

Exon 7 (g.15753T>G)
GTCTGTCTTGACTGGACATGTGGCTTTCCTGATGCACGCATAGAGGAAGGATGG
TAAAAAGGTGCTGATTTTAATTTTCCACATCTTTCTCCACTCAGCGTCTTTGGGG
CCTACAGCATGGATGTGATCACTAGCACATCATTTGGAGTGAACATCGACTCT
CTCAACAATCCACAAGACCCCTTTGTGGAAAACACCAAGAAGCTTTTAAGATT
TGATTTTTTGGATCCATTCTTTCTCTCAATAAGTATGTGGACTACTATTTCCTTTT
ATTTATCTTT→GCTCTCTTAAAAATAACTGCTTTATTGAGATATAAATCACCATGT
AATTCATCCACTTAAAATATACAGTTCAGTGATTTGTAGTACATTTGAAGATATGT
GTGACCATCATC

SEQ ID NO:136

Exon 9
GGAGATCAAGGACCACGCTTGTGATTTACTTCTGACTTCAGGAGCCACTTTCTG
TCAGTGAAATTTCTCTTTTTGCTTCTAGCACCGAGTGGATTTCCTTCAGCTGATG
ATTGACTCTCAGAATTCAAAAGAAACTGAGTCCCACAAAGGTAACCAGAGTGT
TTCTGAGGGCTACTTGTGGGGCACTCAGAGGGAAGGCCTTGTTCTGAAAATGTG
CAGGAAGTATTCCAGGATGATGAG

SEQ ID NO:138

CYP3A7
Exon 11 (C1229G Thr409Arg polymorphism)
CCAGTATGAGTTGTTCTCTGGAACTTCTAACAGTTCAACAGTACTACATGGACTG
AGTTAAAAGTTAATTCAAAAATCTCAATTTATCCAAATCTGTTTCTTTCTTTTCAGG
CACCACCCACCTATGATACTGTGCTACAGTTGGAGTATCTTGACATGGTGGT
AATGAAACACTCAGATTATTCCCAGTTGCTATGAGACTTGAGAGGGTCTGCAA
AAAAGATGTTGAAATCAATGGGATGTTTATTCCCAAAGGGGTGGTGGTGATGA
TTCCAAGCTATGTTCTTCATCATGACCCAAAGTACTGGAC→GAGAGCCTGAGA
AGTTCCTCCCTGAAAGGTAGGAGGCCCCTGGGAAGGGAGCCCTCCCTGAACC
AGCCTGGTTCAAGCATATTCTGCCT

Fig. 6

SEQ ID NO:143

CYP3A4
Exon 4 (Primers 3A4-52F and 3A4-100R)
<u>AGTCTGGCTTCCTGGGTTGGGCT</u>CCAGCTGTAGAATAAGGCTGTTGATGTTTAA
TCAACTCTGTTTTTTTCACAC<u>AG</u>CTTTTATGATGGTCAACAGCCTGTGCTGGCTA
TCACAGATCCTGACATGATCAAAACAGTGCTAGTGAAAGAATGTTATTCTGTCT
TCACAAACCGGAGG<u>GT</u>AAGCATTCATGTGTTGAAATTAAAATACTGATTGATTAA
ATTTATATTTTGAAATTCTTATATATTCATAGACAGTTGCCTAAAAAATGTCCAGG
AAGGTTCCA<u>CGTCCACTTCATCCTGTCCCC</u>    SEQ ID NO:144

Exon 5 (g.13908G>A, R130Q)
<u>CTACAACCATGGAGACCTCC</u>ACAACTGATGTAGGACAAAATGTTTCTGCTTTGAA
CTCT<u>AG</u>CCTTTTGGTCCAGTGGGATTTATGAAAAGTGCCATCTCTATAGCTGAG
GATGAAGAATGGAAGAGATTAC<u>G→</u>AATCATTGCTGTCTCCAACCTTCACCAGT
GGAAAACTCAAGGAG<u>GT</u>ATGAAAATAACATGAGTTTTAATAAGAAACTTAAAGA
AT<u>GAATCTGGTGGGGACAGGTA</u>    SEQ ID NO:146

Exon 6 (g.14292G>A, V170I; g.14304G>C, D174H; g.14323C>T; g.14329G>T; g.14357T>G)
<u>CCCTTTCCAAGGGGTAGTCC</u>ACTGAATTTGAGCTGCCTAAAAATGGTCTTTTATC
TTTATGTACAGAAAACACATCACAAAATTCATTATAAAATGTCACTTACTGCTCCA
TGCTGGGGAAAGCCATGTCCTTCTGGGACTAGAGTCTGCACATTTAACTATGGG
TGGTGTTGTGTTTTGTGCTT<u>AG</u>ATGGTCCCTATCATTGCCCAGTATGGAGATGT
GTTGGTGAGAAATCTGAGGCGGGAAGCAGAGACAGGCAAGCCT<u>G→</u>ATCACC
TTGAAA<u>G→C</u>A<u>GT</u>AAGTAGAAGCGCAGC<u>C→</u>TATGGG<u>G→</u>TTTCTGAGCTGTCAT
GAACCCCTCCAGC<u>T→</u>GGCCTGCCATGGAGCTGATATT<u>CCTGCTGTTGGGTTAT</u>
<u>TCCAGTGACCAGAC</u>    SEQ ID NO:148

Exon10 (g.20230G>A)
<u>CCCAGTGTACCTCTGAATTGC</u>TTTTCTATTCTTTTCCCTTAGGGATTTGAGGGCT
TCACTTAGATTTCTCTTCATCTAAACTGTGATGCCCTACATTGATCTGATTTACCT
AAAAATGTCTTTCCTCTCCTTTC<u>AG</u>CTCTGTCCGATCTGGAGCTCGTGGCCCAAT
CAATTATCTTTATTTTTGCTGGCTATGAAACCACGAGCAGTGTTCTCTCCTTCAT
TATGTATGAACTGGCCACTCACCCTGATGTCCAGCAGAAACTGCAGGAGGAA
ATTGATGCAGTTTTACCCAATAAG<u>GT</u>GAGTGGATG<u>G→</u>ATACATGGAGAAGGAG
GGAGGAGGTGAAACCTTAGCAAAAATGCCTCCTCACCACTTCCAGGAGAATTT
TTATAAAAAGCATAATCACTGATTCTTTCACTGACT<u>CTATGTAGGAAGGCTCTG</u>
SEQ ID NO:159

Exon 11 (g.21867C>T, T363M; g.21868G>A; g.21896C>T, L373F; g.22026C>T,
P416L; g.22041C>T;)
<u>CAGTATGAGTTAGTCTCTGG</u>AGCTCCTAATACTTCATTAGTACTGCATGGACTGA
GTTAAAAGTTAATTCAAAATCTCAATTTATCCAAATCTGTTTCGTTCTTTCC<u>AG</u>GC
ACCACCCACCTATGATACTGTGCTACAGATGGAGTATCTTGACATGGTGGTGA
ATGAAA<u>C→</u>T<u>G→</u>ACTCAGATTATTCCCAATTGCTATGAGA<u>C→</u>TTTGAGAGGGT
CTGCAAAAAAGATGTTGAGATCAATGGGATGTTCATTCCCAAAGGGGTGGTGG
TGATGATTCCAAGCTATGCTCTTCACCGTGACCCAAAGTACTGGACAGAGCCT
GAGAAGTTCCTCCC<u>C→</u>TTGAAAG<u>GT</u>ACAAGG<u>C→</u>TCCCTGGGAAGGGAGCCCTC

Fig. 6 cont.

CCTGAACCAGCCTGGTTCAAGCATATTCTGCCTCTCTTAATCTACAGGACAGTCA
TGTGGTTGTATAATTATTTGCTTGTATTTTTTATATTTAGAGATTTTTTTAATCATCA
AATTGATTATTGTCACACTTTACAAACCATAGACTAGAAAAAAGAAAACTACAGTC
ATCCACAATTCCAACAACTTA<u>CGATGAAGGTCATCAGTTATG</u>

<div align="right">SEQ ID NO:162</div>

Exon 12 (g.23081C>T)
<u>CCTGTGTACTACTAGT*T*GAGGG</u>GTGGCCCCTAAGTAAGAAACCCTAACATGTAA
CTCTTAGGGGTATTATGTCATTAACTTTTTAAAAATCTACCAA<u>C</u>→TGTGGAACC<u>A
GA</u>TTCAGCAAGAAGAACAAGGACAACATAGATCCTTACATATACACACCCTTT
GGAAGTGGACCCAGAAACTGCATTGGCATGAGGTTTGCTCTCATGAACATGAA
ACTTGCTCTAATCAGAGTCCTTCAGAACTTCTCCTTCAAACCTTGTAAAGAAAC
ACAG<u>GT</u>TAGTCAATTTTCTATAAAAATAATGTTGTATTAATAATTCTTTTAACTGA
GTGGTCTGTATTTTTTAAAAAGAATATGCTTGTTTAATCTTTTACTAATTTGTTCTC
TGGGCCAAAGAAT<u>CAATTAGGCCCATCTGTG</u>

<sup>*</sup> this oligonucleotide used for genotyping differs from the genomic sequence at the positions shown in italics <div align="right">SEQ ID NO:163</div>

Exon 13 (g.25925C>T; g.25958T>G)
<u>GGAGTGTCTCACTCACTTTGATGC</u>TATACTTTCTACTTTTGTTTATTTAATGCTTC
TCAATATGCTTGTTTAACTGTTGC<u>AG</u>ATCCCCCTGAAATTAAGCTTAGGAGGAC
TTCTTCAACCAGAAAAACCCGTTGTTCTAAAGGTTGAGTCAAGGGATGGCAC<u>C</u>
→TGTAAGTGGAGCCTGAATTTTCCTAAGGACTTC<u>T</u>→GGCTTTGCTCTTCAAGAA
ATCTGTGCCTGAGAACACCAGAGACCTCAAATTACTTTGTGAATAGAACTCTGAA
AT<u>GAAGATGGGCTTCATCCA</u>

Fig. 6 cont.

POLYMORPHISMS IN THE HUMAN CYP3A4 AND CYP3A7 GENES AND THEIR USE IN DIAGNOSTIC AND THERAPEUTIC APPLICATIONS

FIELD OF THE INVENTION

The present invention relates generally to means and methods of diagnosing and treating the phenotypic spectrum as well as the overlapping clinical characteristics with several forms of inherited abnormal expression and/or function of the cytochrome P-450 (CYP)3A4 and CYP3A7 genes. In particular, the present invention relates to polynucleotides of molecular variant CYP3A4 and CYP3A7 genes which, for example, are associated with abnormal drug response or individual predisposition to several common cancers caused by environmental carcinogens, and to vectors comprising such polynucleotides. Furthermore, the present invention relates to host cells comprising such polynucleotides or vectors and their use for the production of variant CYP3A4 and CYP3A7 proteins. In addition, the present invention relates to variant CYP3A4 and CYP3A7 proteins and antibodies specifically recognizing such proteins. The present invention also concerns transgenic non-human animals comprising the above-described polynucleotide or vectors. Moreover, the present invention relates to methods for identifying and obtaining drug candidates and inhibitors for therapy of disorders related to the malfunction of the CYP3A4 and CYP3A7 genes as well as to methods of diagnosing the status of such disorders. The present invention furthermore provides pharmaceutical and diagnostic compositions comprising the above-described polynucleotides, vectors, proteins, antibodies, and drugs and inhibitors obtainable by the above-described method. Said compositions are particularly useful for diagnosing and treating various diseases with drugs that are substrates, inhibitors or modulators of the CYP3A4 and CYP3A7 genes or their product.

Several documents are cited throughout the text of this specification. Each of the documents cited herein (including any manufacturer's specifications, instructions, etc.) are hereby incorporated herein by reference; however, there is no admission that any document cited is indeed prior art as to the present invention.

BACKGROUND OF THE INVENTION

Members of the cytochrome P-450 (CYP) family of hemoproteins metabolise a wide variety of endogenous substrates such as steroid hormones, and of xenobiotics including carcinogens, toxins and drugs (1,2). Of the human CYP proteins, those of the CYP3A subfamily are of a major importance, since collectively, they are by far the most abundant of all the human CYP isoforms. Moreover, their substrate specificity is extremely broad; accordingly, many structurally diverse compounds are, exclusively or to some extent, substrates for CYP3A proteins. Based on the data available it is generally assumed that all CYP3A isoforms have similar substrate spectra; however, limited studies indicate the possibility of differences (3). All CYP3A isoforms are localized in organs of particular importance to drug disposition (gastrointestinal tract, kidney and liver).

At least three functional CYP3A proteins exist in humans. The CYP3A4 monooxygenase is the predominant cytochrome P450 in human liver and small bowel. The protein displays a broad substrate specificity and it metabolises more than 60% of all drugs that are currently in use, including contraceptive steroids, antidepressants, benzodiazepines, immunosuppressive agents, imidazole antimicotics, and macrolide antibiotics (4,5). In addition, CYP3A4 plays a major role in the protection from environmental toxins. For example, the protein metabolizes aflatoxin B1, which has been implicated in the etiology of liver cancer, which is a major cause of premature death in many areas of Africa and Asia. Aflatoxin B1 is a mycotoxin produced by species of *Aspergillus*, and human exposure results principally from the ingestion of stored foodstuffs contaminated with the mold. Carcinogenicity is associated with its conversion to 8,9-oxide by the hepatic cytochrome P450-dependent monooxygenase system. Forrester et al. (6) found that the rates of metabolic activation of aflatoxin B1 were highly correlated with the level of proteins of the CYP3A gene family in the microsomes. Furthermore, Paolini et al. (7) found significant increases in CYP3A in the lungs of rats treated with high doses of beta-carotene. Consequently, it was proposed that correspondingly high levels of CYP3A4 in humans would predispose an individual to cancer risk from the bioactivated tobacco-smoke procarcinogens, thus explaining the cocarcinogenic effect of beta-carotene in smokers. All this implies that individual variation in the CYP3A4 activity could influence the efficacy of a variety of drug therapies as well as the individual predisposition to several major cancers caused by environmental carcinogens.

A considerable variation in the CYP3A4 content and catalytic activity has been, indeed, described in the general population. For example, the metabolic clearance of the gene substrates exhibits a unimodal distribution with up to 20-fold interindividual variability. The activities of the CYP3A4 protein in liver biopsies vary up to 30-fold (8). Furthermore, many common drugs alter the expression levels of the gene (induction or repression) and the extent of this phenomenon is individually variable. The inducers of CYP3A4 expression include commonly used drugs such as the glucocorticoid dexamethasone, the antibiotic rifampicin, and the antimycotic clotrimazole. The inducibility of CYP3A4 expression, combined with the diverse renge of substrates, creates a potential for potentially harmful drug interactions involving this isozyme in patients undergoing therapies with multiple drugs.

CYP3A3 is a very closely related isoform to CYP3A4 (>more than 98% cDNA sequence similarity), but it is not known whether this reflects a separate gene product or an allelic variant. By contrast, CYP3A5 is a gene distinct from CYP3A4 and it is expressed polymorphically both in the adult and fetal liver and in the kidney and intestine. In adult Caucasians, the mRNA and the protein were detected in the liver of 10 to 30% of samples, while the protein was detected in the kidney and intestine of 70% of subjects (Ref. (9) and references therein). A point mutation described in the CYP3A5 gene which possibly results in the synthesis of an unstable protein, may account for the polymorphic expression of this enzyme (9). CYP3A7 is the third functional CYP3A isoform. CYP3A7 was originally isolated from a fetal liver but it was subsequently found in 54% of adult livers (10).

Tests to estimate the inducibility and the activity of CYP3A isozymes in an individual patient would be of obvious relevance for the optimization of therapies with drugs which are their substrates, and for the prevention of the associated side effects. Direct estimates of the activities of CYP3A isozymes in liver biopsies are possible but impracticable for both ethical and cost reasons. The indirect in vivo tests of CYP3A4 activity such as the erythromycin breath test or the 6-β-hydroxycortisol test pose ethical problems such as the invasive administration of undesirable probe substances and they are obviously unsuited for routine testing. In addition, the lack of correlation between these tests questions their informative value regarding the CYP3A4 activity (11).

A major portion (83%) of the interindividual CYP3A4 variability has been attributed to genetic factors (12). The establishment of a genetic test for the activity of CYP3A4 and of the other CYP3A isozymes should be possible, assuming the prior identification of those factors. Genetic variance affecting the activity and the expression of CYP3A isozymes could be localized in the genes itself, or in one or more of their regulators. A comparison of the three originally published sequences of the best characterized CYP3A gene, CYP3A4, suggested the existence of polymorphisms affecting the amino acid sequence of the CYP3A4 protein (13). Unfortunately, this observation has not been, to our knowledge, confirmed in the general population. More recently, a polymorphism (CYP3A4-W) has been described in the nifedipine-specific response element of the CYP3A4 promoter (14). Its presence associates with a more advanced prostate tumor stage (14). Felix et al. (15) examined this polymorphism in 99 de novo and 30 treatment-related leukemias. In all treatment-related cases, there was prior exposure to one or more anti-cancer drugs metabolized by CYP3A, such as epipodophyllotoxins. These data suggest that individuals with the CYP3A4-W polymorphism may be at increased risk for treatment-related leukemia and that epipodophyllotoxin metabolism by CYP3A4 may contribute to the secondary cancer risk. At present it is unclear if the polymorphism influences the expressivity or inducibility of the CYP3A4 protein. A first published analysis suggests that it has no effect on the basal expression level of CYP3A4 (8). A point mutation was described in the CYP3A5 (9), whereas no mutations have been reported in CYP3A7.

Experiments with amino acid exchanges artificially introduced into the CYP3A4 gene indicate that the function of the family members may be quite sensitive to amino acid exchanges (16-21). Besides amino acid exchanges, silent polymorphisms and those localized in untranslated or intronic sequences also could influence the expression level of these genes. Alternatively, such polymorphisms could serve as markers for nearby, unidentified polymorphisms. This effect is known as linkage, i.e. defined polymorphisms serve as markers for phenotypes that they are not causative for.

A major breakthrough in the understanding of the CYP3A expression and inducibility took place in 1998 when three research groups independently showed that the expression of CYP3A4 is regulated by a member of the orphan nuclear receptor family termed PXR (pregnane X receptor), or PAR (22-24). Upon treatment with inducers of CYP3A4, PXR binds to the rifampicin/dexamethasone response element in the CYP3A4 promoter as a heterodimer with the 9-cis retinoic acid receptor (RXR). Northern blot analysis detected most abundant expression of hPXR in liver, colon, and small intestine, i.e. in the major organs expressing CYP3A4. The available evidence suggests that human PXR serves as a key transcriptional regulator of the CYP3A4 gene. A recent report describes the induction of CYP3A7 mediated by PXR suggesting that all members of the family may be regulated by this common transcriptional activator (25).

It is clear that naturally occurring mutations, if they exist can have effects on drug metabolization and efficacy of therapies with drugs, in particular in cancer treatment. It is unknown, however, how many of such variations exist, and with what frequency and at what positions in the human CYP3A4 and CYP3A7 genes.

Accordingly, means and methods for diagnosing and treating a variety of forms of individual drug intolerability and inefficacy of drug therapy which result from CYP3A4 and/or CYP3A7 gene polymorphisms that interfere e.g., with chemotherapeutic treatment of diseases, in particular cancer, were hitherto not available but are nevertheless highly desirable.

Thus, the technical problem of the present invention is to comply with the needs described above.

The solution to this technical problem is achieved by providing the embodiments characterized in the claims.

SUMMARY OF THE INVENTION

The present invention is based on the finding of novel, so far unknown variations in the nucleotide sequences of the CYP3A4 and CYP3A7 genes and the population distribution of these alleles. Based upon the knowledge of these novel sequences diagnostic tests and reagents for such tests were designed for the specific detection and genotyping of CYP3A4 and CYP3A7 alleles in humans, including homozygous as well as heterozygous, frequent as well as rare alleles of the CYP3A4 and CYP3A7 genes. The determination of the CYP3A4 and/or CYP3A7 gene allele status of humans with such tests is useful for the optimization of therapies with the numerous substrates of CYP3A4 and CYP3A7. It may also be useful in the determination of the individual predisposition to several common cancers caused by environmental carcinogens.

In a first embodiment, the invention provides polynucleotides of molecular variant CYP3A4 and CYP3A7 genes and embodiments related thereto such as vectors, host cells, variant CYP3A4 and CYP3A7 proteins and methods for producing the same.

In yet another embodiment, the invention provides methods for identifying and obtaining drug candidates and inhibitors of CYP3A4 and CYP3A7 for therapy of disorders related to acquired drug hypo- or hypersensitivity as well as methods of diagnosing the status of such disorders.

In a further embodiment, the invention provides pharmaceutical and diagnostic compositions comprising the above-described polynucleotides, vectors containing the same, proteins, antibodies thereto, and drugs and inhibitors obtainable by the above-described method.

The pharmaceutical and diagnostic compositions, methods and uses of the invention are useful for the diagnosis and treatment of cancer and other diseases the therapy of which is dependent on drug treatment and tolerance. The novel variant forms of CYP3A4 and CYP3A7 genes according to the invention provide the potential for the development of a pharmacodynamic profile of drugs for a given patient.

DESCRIPTION OF THE INVENTION

The finding and characterization of variations in the CYP3A4 and CYP3A7 genes, and diagnostic tests for the discrimination of different CYP3A4 and CYP3A7 alleles in human individuals provide a very potent tool for improving the therapy of diseases with drugs that are targets of the CYP3A4 or CYP3A7 gene product, and whose metabolization is therefore dependent on CYP3A4 or CYP3A7. The diagnosis of the individual allelic CYP3A4 and CYP3A7 status permits a more focused therapy, e.g., by opening the possibility to apply individual dose regimens of drugs. It may also be useful as prognostic tool for therapy outcome. Furthermore, diagnostic tests to genotype CYP3A4 and CYP3A7, and novel CYP3A4 and CYP3A7 variants, will not only improve therapy with established drugs and help to correlate genotypes with drug activity or side effects. These tests and sequences also provide reagents for the development of novel inhibitors that specifically modulate the activity of the individual types of CYP3A4 and CYP3A7. Expression in yeast, for example, of three allelic cDNAs encoding human liver CYP3A4 and methods for testing the binding properties and catalytic activities of their gene products have been described in (13).

Thus, the present invention provides a novel way to exploit molecular biology and pharmalogical research for drug therapy while bypassing their potential detrimental effects which are due to expression of variant CYP3A4 and CYP3A7 genes.

Accordingly, the invention relates to a polynucleotide selected from the group consisting of:

(a) a polynucleotide having the nucleic acid sequence of SEQ ID NO: 54, 55, 58, 59, 62, 63, 66, 67, 70, 71, 74, 75, 78, 79, 82, 83, 86, 87, 90, 91, 94, 95, 98, 99, 102, 103, 106, 107, 110, 111, 118, 119, 122, 123, 126, 127, 128, 134, 138, 144, 146, 148, 150, 151, 152, 153, 154, 156, 157, 159, 161, 162, 163, 164 or 171;

(b) a polynucleotide encoding a polypeptide having the amino acid sequence of any one of SEQ ID NO: 129, 135, 139, 145, 147, 155, 158, 160 or 172;

(c) a polynucleotide encoding a CYP3A4 or CYP3A7 polypeptide, wherein said polynucleotide is having at a position corresponding to any one of position 6004, 13908, 14292, 14304, 14323, 14329, 14357, 15753, 20230, 21867, 21868, 21896, 22026, 22041, 23081, 23172, 25925 or 25958 of the CYP3A4 gene (Accession No: AF280107, whereby the nucleotide A of the first ATG encoding the CYP3A4 protein has been taken as position 1) or at a position corresponding to position 1229 of the CYP3A7 (Accession No: gi4503232) a nucleotide exchange, a nucleotide deletion, an additional nucleotide or an additional nucleotide and a nucleotide exchange, wherein said nucleotide deletion at a position corresponding to position 23172 is not resulting in an M to T amino acid substitution or is not a T to C nucleotide exchange;

(d) a polynucleotide encoding an CYP3A4 or CYP3A7 polypeptide, wherein said polynucleotide is having at a position corresponding to any one of position 6004, 13908, 14292, 20230 or 21868 of the CYP3A4-gene (Accession No: AF280107, whereby the nucleotide A of the first ATG encoding the CYP3A4 protein has been taken as position 1) an A, at a position corresponding to any one of position 14323, 14329, 21867, 21896, 22026, 22041, 23081 or 25925 of the CYP3A4 gene (Accession No: AF280107, whereby the nucleotide A of the first ATG encoding the CYP3A4 protein has been taken as position 1) a T, at a position corresponding to any one of position 14357, 15753 or 25958 of the CYP3A4 gene (Accession No: AF280107, whereby the nucleotide A of the first ATG encoding the CYP3A4 protein has been taken as position 1) a G, at a position corresponding to any one of position 14304 of the CYP3A4 gene (Accession No: AF280107, whereby the nucleotide A of the first ATG encoding the CYP3A4 protein has been taken as position 1) a C or at a position corresponding to position 1229 of the CYP3A7 gene (Accession No: gi4503232) a G;

(e) a polynucleotide encoding an CYP3A4 polypeptide, wherein said polypeptide comprises an amino acid substitution at any one of position 56, 130, 170, 174, 363, 373, 416 or 445 of the CYP3A4 polypeptide (Accession No: AF280107), wherein said substitution at a position corresponding to position 445 is not M to T; and (f) a polynucleotide encoding an CYP3A4 or CYP3A7 polypeptide, wherein said polypeptide comprises an amino acid substitution of G to D at position 56, R to Q at position 130, V to I at position 170, D to H at position 174, T to M at position 363, L to F at position 373 or P to L at position 416 of the CYP3A4 polypeptide (Accession No: AF280107) or T to R at position 409 of the CYP3A7 polypeptide (Accession No: gi4503232).

In the context of the present invention the term "molecular variant" CYP3A4 or CYP3A7 gene or protein as used herein means that said CYP3A4 or CYP3A7 gene or protein differs from the wild type CYP3A4 or CYP3A7 gene or protein by way of nucleotide substitution(s), addition(s) and/or deletion(s) (Genomic sequences of the CYP3A4, CYP3A7 gene are described, for example Bork, J Biol Chem 264 (1989), 910-9; Hashimoto, Eur J Biochem 218 (1993), 585-95; Beaune, Proc Natl Acad. Sci USA 83 (1986), 8064-8; Malowa, Proc Natl Acad Sci USA 83 (1986), 5311-5; Accession numbers: M14096, J04449, X12387, M18907. The numbering of the polymorphisms refers to the sequence M14096; for CYP3A7: the reference sequence is described in Komori, J Biochem (Tokyo) 105 (1989), 161-3; Accession number: gi4503232. Preferably, said nucleotide substitution(s) result(s) in a corresponding change in the amino acid sequence of the CYP3A4 or CYP3A7 protein.

The term "corresponding" as used herein means that a position is not only determined by the number of the preceding nucleotides and amino acids, respectively. The position of a given nucleotide or amino acid in accordance with the present invention which may be deleted, substituted or comprise one or more additional nucleotide(s) may vary due to deletions or additional nucleotides or amino acids elsewhere in the gene or the polypeptide. Thus, under a "corresponding position" in accordance with the present invention it is to be understood that nucleotides or amino acids may differ in the indicated number but may still have similar neighboring nucleotides or amino acids. Said nucleotides or amino acids which may be exchanged, deleted or comprise additional nucleotides or amino acids are also comprised by the term "corresponding position". Said nucleotides or amino acids may for instance together with their neighbors form sequences which may be involved in the regulation of gene expression, stability of the corresponding RNA or RNA editing, as well as encode functional domains or motifs of the protein of the invention.

In accordance with the present invention, the mode and population distribution of novel so far unidentified genetic variations in the CYP3A4 and CYP3A7 gene have been analyzed by sequence analysis of relevant regions of the human CYP3A4 and CYP3A7 genes from many different individuals. It is a well known fact that genomic DNA of individuals, which harbor the individual genetic makeup of all genes, including CYP3A4 and CYP3A7 can easily be purified from individual blood samples. These individual DNA samples are then used for the analysis of the sequence composition of the CYP3A4 and CYP3A7 gene alleles that are present in the individual which provided the blood sample. The sequence analysis was carried out by PCR amplification of relevant regions of the CYP3A4 and CYP3A7 genes, subsequent purification of the PCR products, followed by automated DNA sequencing with established methods (ABI dyeterminator cycle sequencing).

One important parameter that had to be considered in the attempt to determine the individual CYP3A4 and/or CYP3A7 genotype and identify novel CYP3A4 or CYP3A7 variants by direct DNA-sequencing of PCR-products from human blood genomic DNA is the fact that each human harbors (usually, with very few abnormal exceptions) two gene copies of each autosomal gene (diploidy). Because of that, great care had to be taken in the evaluation of the sequences to be able to identify unambiguously not only homozygous sequence variations but also heterozygous variations. The details of the different steps in the identification and characterization of novel CYP3A4 and CYP3A7 gene polymorphisms (homozygous and heterozygous) are described in the examples below.

Sequence data for some of the mutations in the CYP3A4 and CYP3A7 genes detected in accordance with the present invention are illustrated in FIG. 4 (indicated by an arrow). The methods of the mutation analysis followed standard protocols and are described in detail in the examples. In general such methods to be used in accordance with the present invention for evaluating the phenotypic spectrum as well as the overlapping clinical characteristics with other forms of drug metabolization and altered tolerance to drugs in patients with mutations in the CYP3A4 or CYP3A7 gene encompass for example haplotype analysis, single-strand conformation polymorphism analysis (SSCA), PCR and direct sequencing. On the basis of thorough clinical characterization of many patients the phenotypes can then be correlated to these mutations as well as to mutations that had been described earlier.

As is evident to the person skilled in the art this new molecular genetic knowledge can now be used to exactly characterize the genotype of the index patient and of his family where a given drug takes an unusual effect.

Over the past 20 years, genetic heterogeneity has been increasingly recognized as a significant source of variation in drug response. Many scientific communications (Meyer, Ann. Rev. Pharmacol. Toxicol. 37 (1997), 269-296 and West, J. Clin. Pharmacol. 37 (1997), 635-648) have clearly shown that some drugs work better or may even be highly toxic in some patients than in others and that these variations in patient's responses to drugs can be related to molecular basis. This "pharmacogenomic" concept spots correlations between responses to drugs and genetic profiles of patient's (Marshall, Nature Biotechnology, 15 (1997), 954-957; Marshall, Nature Biotechnology, 15 (1997), 1249-1252).

In this context of population variability with regard to drug therapy, pharmacogenomics has been proposed as a tool useful in the identification and selection of patients which can respond to a particular drug without side effects. This identification/selection can be based upon molecular diagnosis of genetic polymorphisms by genotyping DNA from leukocytes in the blood of patient, for example, and characterization of disease (Bertz, Clin. Pharmacokinet. 32 (1997), 210-256; Engel, J. Chromatogra. B. Biomed. Appl. 678 (1996), 93-103). For the providers of health care, such as health maintenance organizations in the US and government public health services in many European countries, this pharmacogenomics approach can represent a way of both improving health care and reducing overheads because there is a large cost to unnecessary therapies, ineffective drugs and drugs with side effects.

The mutations in the variant CYP3A4 and CYP3A7 genes sometime result in amino acid deletion(s), insertion(s) and in particular in substitution(s) either alone or in combination. It is of course also possible to genetically engineer such mutations in wild type genes or other mutant forms. Methods for introducing such modifications in the DNA sequence of CYP3A4 or CYP3A7 gene are well known to the person skilled in the art; see, e.g., Sambrook, Molecular Cloning A Laboratory Manual, Cold Spring Harbor Laboratory (1989) N.Y.

In a preferred embodiment of the invention, the above described polynucleotide encodes a variant CYP3A4 or CYP3A7 protein or fragment thereof, e.g., comprising one or more epitopes of the amino acid sequence encoded by SEQ ID NOS: 129, 135, 139, 145, 147, 149, 155, 158 or 160.

For the investigation of the nature of the alterations in the amino acid sequence of the CYP3A4 and CYP3A7 proteins computer programs may be used such as BRASMOL that are obtainable from the Internet. Furthermore, folding simulations and computer redesign of structural motifs can be performed using other appropriate computer programs (Olszewski, Proteins 25 (1996), 286-299; Hoffman, Comput. Appl. Biosci. 11 (1995), 675-679). Computers can be used for the conformational and energetic analysis of detailed protein models (Monge, J. Mol. Biol. 247 (1995), 995-1012; Renouf, Adv. Exp. Med. Biol. 376 (1995), 37-45). These analysis can be used for the identification of the influence of a particular mutation on binding and/or metabolization of drugs.

Usually, said amino acid deletion, addition or substitution in the amino acid sequence of the protein encoded by the polynucleotide of the invention is due to one or more nucleotide substitution, insertion or deletion, or any combinations thereof. Preferably said nucleotide substitution, insertion or deletion results in an amino acid substitution of Gly56 to Asp, Arg130 to Gln, Val170 to Ile, Asp174 to His, Thr363 to Met, Leu373 to Phe or Pro416 to Leu in the CYP3A4 gene and/or Thr409 to Arg in exon 11 of the CYP3A7 gene.

The polynucleotide of the invention may further comprise at least one nucleotide and optionally amino acid deletion, addition and/or substitution other than those specified hereinabove, for example those described in the prior art; e.g., (13). This embodiment of the present invention allows the study of synergistic effects of the mutations in the CYP3A4 or CYP3A7 gene on the pharmalogical profile of drugs in patients who bear such mutant forms of the gene or similar mutant forms that can be mimicked by the above described proteins. It is expected that the analysis of said synergistic effects provides deeper insights into drug tolerant or sensitive phenotypes of certain forms of cancer and other diseases. From said deeper insight the development of diagnostic and pharmaceutical compositions related to cancer will greatly benefit.

Thus, in a preferred embodiment, the present invention relates to polynucleotides of molecular variant CYP3A4 and CYP3A7 genes, wherein the nucleotide deletion, addition and/or substitution result in altered expression of the variant CYP3A4 or CYP3A7 gene compared to the corresponding wild type gene.

The polynucleotide of the invention may be, e.g., DNA, cDNA, genomic DNA, RNA or synthetically produced DNA or RNA or a recombinantly produced chimeric nucleic acid molecule comprising any of those polynucleotides either alone or in combination. Preferably said polynucleotide is part of a vector, particularly plasmids, cosmids, viruses and bacteriophages used conventionally in genetic engineering that comprise a polynucleotide of the invention. Such vectors may comprise further genes such as marker genes which allow for the selection of said vector in a suitable host cell and under suitable conditions.

In a further preferred embodiment of the vector of the invention, the polynucleotide of the invention is operatively linked to expression control sequences allowing expression in prokaryotic or eukaryotic cells. Expression of said polynucleotide comprises transcription of the polynucleotide, preferably into a translatable mRNA. Regulatory elements ensuring expression in eukaryotic cells, preferably mammalian cells, are well known to those skilled in the art. They usually comprise regulatory sequences ensuring initiation of transcription and optionally poly-A signals ensuring termination of transcription and stabilization of the transcript. Additional regulatory elements may include transcriptional as well as translational enhancers. Possible regulatory elements permitting expression in prokaryotic host cells comprise, e.g., the lac, trp or tac promoter in *E. coli*, and examples for regulatory elements permitting expression in eukaryotic host cells are the AOX1 or GAL1 promoter in yeast or the CMV-, SV40-, RSV-promoter (Rous sarcoma virus), CMV-enhancer, SV40-enhancer or a globin intron in mammalian and other animal cells. Beside elements which are responsible for the initiation of transcription such regulatory elements may also comprise transcription termination signals, such as the SV40-poly-A site or the tk-poly-A site, downstream of the polynucleotide. In this context, suitable expression vectors are known in the art such as Okayama-Berg cDNA expression vector pcDV1 (Pharmacia), pCDM8, pRc/CMV, pcDNA1, pcDNA3 (Invitrogene), pSPORT1 (GIBCO BRL). Preferably, said vector is an expression vector and/or a gene transfer or targeting vector. Expression vectors derived from viruses such as retroviruses, vaccinia virus, adeno-associated virus, herpes viruses, or bovine papilloma virus, may be used for delivery of the polynucleotides or vector of the invention into targeted cell population. Methods which are well known to those skilled in the art can be used to construct recombinant viral vectors; see, for example, the techniques described in Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1994). Alternatively, the polynucleotides and vectors of the invention can be reconstituted into liposomes for delivery to target cells.

The present invention furthermore relates to host cells transformed with a polynucleotide or vector of the invention. Said host cell may be a prokaryotic or eukaryotic cell; see supra. The polynucleotide or vector of the invention which is present in the host cell may either be integrated into the genome of the host cell or it may be maintained extrachromosomally. In this respect, it is also to be understood that the recombinant DNA molecule of the invention can be used for "gene targeting" and/or "gene replacement", for restoring a mutant gene or for creating a mutant gene via homologous recombination; see for example Mouellic, Proc. Natl. Acad. Sci. USA, 87 (1990), 4712-4716; Joyner, Gene Targeting, A Practical Approach, Oxford University Press.

The host cell can be any prokaryotic or eukaryotic cell, such as a bacterial, insect, fungal, plant, animal or human cell. Preferred fungal cells are, for example, those of the genus *Saccharomyces*, in particular those of the species *S. cerevisiae*. The term "prokaryotic" is meant to include all bacteria which can be transformed or transfected with a polynucleotide for the expression of a variant CYP3A4 or CYP3A7 protein or fragment thereof. Prokaryotic hosts may include gram negative as well as gram positive bacteria such as, for example, *E. coli, S. typhimurium, Serratia marcescens* and *Bacillus subtilis*. A polynucleotide coding for a mutant form of CYP3A4 and CYP3A7 variant proteins can be used to transform or transfect the host using any of the techniques commonly known to those of ordinary skill in the art. Methods for preparing fused, operably linked genes and expressing them in bacteria or animal cells are well-known in the art (Sambrook, supra). The genetic constructs and methods described therein can be utilized for expression of variant CYP3A4 and CYP3A7 proteins in, e.g., prokaryotic hosts. In general, expression vectors containing promoter sequences which facilitate the efficient transcription of the inserted polynucleotide are used in connection with the host. The expression vector typically contains an origin of replication, a promoter, and a terminator, as well as specific genes which are capable of providing phenotypic selection of the transformed cells. The transformed prokaryotic hosts can be grown in fermentors and cultured according to techniques known in the art to achieve optimal cell growth. The proteins of the invention can then be isolated from the grown medium, cellular lysates, or cellular membrane fractions. The isolation and purification of the microbially or otherwise expressed polypeptides of the invention may be by any conventional means such as, for example, preparative chromatographic separations and immunological separations such as those involving the use of monoclonal or polyclonal antibodies.

Thus, in a further embodiment the invention relates to a method for the production of variant CYP3A4 and CYP3A7 proteins and fragments thereof comprising culturing a host cell as defined above under conditions allowing the expression of the protein and recovering the produced protein or fragment from the culture.

In another embodiment the present invention relates to a method for producing cells capable of expressing a variant CYP3A4 and/or CYP3A7 gene comprising genetically engineering cells with the polynucleotide or with the vector of the invention. The cells obtainable by the method of the invention can be used, for example, to test drugs according to the methods described in Sambrook, Fritsch, Maniatis (1989). Molecular cloning: a laboratory manual. Cold Spring Harbour Laboratory press, Cold Spring Harbour; Peyronneau, Eur J Biochem 218 (1993), 355-61; Yamazaki, Carcinogenesis 16 (1995), 2167-2170. Furthermore, the cells can be used to study known drugs and unknown derivatives thereof for their ability to complement loss of drug efficacy caused by mutations in the CYP3A4 or CYP3A7 gene. For these embodiments the host cells preferably lack a wild type allele, preferably both alleles of the CYP3A4 and/or CYP3A7 gene and/or have at least one mutated from thereof. Alternatively, strong overexpression of a mutated allele over the normal allele and comparison with a recombinant cell line overexpressing the normal allele at a similar level may be used as a screening and analysis system. The cells obtainable by the above-described method may also be used for the screening methods referred to herein below.

Furthermore, the invention relates to variant CYP3A4 and CYP3A7 proteins and fragments thereof encoded by a polynucleotide according to the invention or obtainable by the above-described methods or from cells produced by the method described above. In this context it is also understood that the variant CYP3A4 and CYP3A7 proteins according to the invention may be further modified by conventional methods known in the art. By providing the variant CYP3A4 and CYP3A7 proteins according to the present invention it is also possible to determine the portions relevant for their biological activity or inhibition of the same.

The present invention furthermore relates to antibodies specifically recognizing a variant CYP3A4 or CYP3A7 protein according to the invention. Advantageously, the antibody specifically recognizes an epitope containing one or more amino acid substitution(s) as defined above Antibodies against the variant CYP3A4 or CYP3A7 protein of the invention can be prepared by well known methods using a purified protein according to the invention or a (synthetic) fragment derived therefrom as an antigen. Monoclonal antibodies can be prepared, for example, by the techniques as originally described in Köhler and Milstein, Nature 256 (1975), 495, and Galfré, Meth. Enzymol. 73 (1981), 3, which comprise the fusion of mouse myeloma cells to spleen cells derived from immunized mammals. The antibodies can be monoclonal antibodies, polyclonal antibodies or synthetic antibodies as well as fragments of antibodies, such as Fab, Fv or scFv fragments etc. Furthermore, antibodies or fragments thereof to the aforementioned polypeptides can be obtained by using methods which are described, e.g., in Harlow and Lane "Antibodies, A Laboratory Manual", CSH Press, Cold Spring Harbor, 1988. These antibodies can be used, for example, for the immunoprecipitation and immunolocalization of the variant CYP3A4 and CYP3A7 proteins of the invention as well as for the monitoring of the presence of such variant CYP3A4 and CYP3A7 proteins, for example, in transgenic organisms, and for the identification of compounds interacting with the proteins according to the invention. For example, surface plasmon resonance as employed in the BIAcore system can be used to increase the efficiency of phage antibodies which bind to an epitope of the protein of the invention (Schier, Human Antibodies Hybridomas 7 (1996), 97-105; Malmborg, J. Immunol. Methods 183 (1995), 7-13).

Furthermore, the present invention relates to nucleic acid molecules which represent or comprise the complementary strand of any of the above described polynucleotides or a part thereof, thus comprising at least one nucleotide difference compared to the corresponding wild type CYP3A4 and CYP3A7 gene nucleotide sequences specified by the above described nucleotide substitutions, deletions and additions. Such a molecule may either be a deoxyribonucleic acid or a ribonucleic acid. Such molecules comprise, for example, antisense RNA. These molecules may furthermore be linked to sequences which when transcribed code for a ribozyme thereby producing a ribozyme which specifically cleaves transcripts of polynucleotides according to the invention.

Furthermore, the present invention relates to a vector comprising a nucleic acid molecule according to the invention. Examples for such vectors are described above. Preferably, the nucleic acid molecule present in the vector is operatively linked to regulatory elements permitting expression in prokaryotic or eukaryotic host cells; see supra.

The present invention also relates to a method for the production of a transgenic non-human animal, preferably transgenic mouse, comprising introduction of a polynucleotide or vector of the invention into a germ cell, an embryonic cell, stem cell or an egg or a cell derived therefrom. The non-human animal can be used in accordance with the method of the invention described below and may be a non-transgenic healthy animal, or may have a disorder, preferably a disorder caused by at least one mutation in the CYP3A4 and/or CYP3A7 gene. Such transgenic animals are well suited for, e.g., pharmacological studies of drugs in connection with variant forms of the above described variant CYP3A4 and CYP3A7 proteins since these proteins or at least their functional domains are conserved between species in higher eukaryotes, particularly in mammals. Production of transgenic embryos and screening of those can be performed, e.g., as described by A. L. Joyner Ed., Gene Targeting, A Practical Approach (1993), Oxford University Press. The DNA of the embryos can be analyzed using, e.g., Southern blots with an appropriate probe.

The invention also relates to transgenic non-human animals such as transgenic mouse, rats, hamsters, dogs, monkeys, rabbits, pigs, C. elegans and fish such as torpedo fish comprising a polynucleotide or vector of the invention or obtained by the method described above, preferably wherein said polynucleotide or vector is stably integrated into the genome of said non-human animal, preferably such that the presence of said polynucleotide or vector leads to the expression of the variant CYP3A4 and/or CYP3A7 gene of the invention. It may have one or several copies of the same or different polynucleotides of the variant CYP3A4 or CYP3A7 gene. This animal has numerous utilities, including as a research model for drug tolerability and therefore, presents a novel and valuable animal in the development of therapies, treatment, etc. for diseases caused by deficiency or failure of drug metabolization in the cell. Accordingly, in this instance, the mammal is preferably a laboratory animal such as a mouse or rat.

Preferably, the transgenic non-human animal of the invention further comprises at least one inactivated wild type allele of the CYP3A4 and/or CYP3A7 gene. This embodiment allows for example the study of the interaction of various variant forms of CYP3A4 and CYP3A7 proteins. It might be also desirable to inactivate CYP3A4 and/or CYP3A7 gene expression or function at a certain stage of development and/or life of the transgenic animal. This can be achieved by using, for example, tissue specific, developmental and/or cell regulated and/or inducible promoters which drive the expression of, e.g., an antisense or ribozyme directed against the RNA transcript of the CYP3A4 or CYP3A7 gene; see also supra. A suitable inducible system is for example tetracycline-regulated gene expression as described, e.g., by Gossen and Bujard (Proc. Natl. Acad. Sci. 89 USA (1992), 5547-5551) and Gossen et al. (Trends Biotech. 12 (1994), 58-62). Similar, the expression of the variant CYP3A4 and CYP3A7 gene may be controlled by such regulatory elements.

With the variant CYP3A4 and CYP3A7 polynucleotides and proteins and vectors of the invention, it is now possible to study in vivo and in vitro the efficiency of drugs in relation to particular mutations in the CYP3A4 or CYP3A7 gene of a patient and the affected phenotype. Furthermore, the variant CYP3A4 and CYP3A7 proteins of the invention can be used to determine the pharmacological profile of drugs and for the identification and preparation of further drugs which may be more effective for the treatment of, e.g., cancer, in particular for the amelioration of certain phenotypes caused by the respective mutations such as those described above.

Thus, a particular object of the present invention concerns drug/pro-drug selection and formulation of pharmaceutical compositions for the treatment of diseases which are amenable to chemotherapy taking into account the polymorphism of the variant form of the CYP3A4 or CYP3A7 gene that cosegregates with the affected phenotype of the patient to be treated. This allows the safe and economic application of drugs which for example were hitherto considered not appropriate for therapy of, e.g., cancer due to either their side effects in some patients and/or their unreliable pharmalogical profile with respect to the same or different phenotype(s) of the disease. The means and methods described herein can be used, for example, to improve dosing recommendations and allows the prescriber to anticipate necessary dose adjustments depending on the considered patient group.

In a further embodiment the present invention relates to a method of identifying and obtaining an CYP3A4 or CYP3A7 inhibitor capable of modulating the activity of a molecular variant of the CYP3A4 or CYP3A7 gene or its gene product comprising the steps of (a) contacting the variant CYP3A4 or CYP3A7 protein or a cell expressing a molecular variant gene comprising a polynucleotide of the invention in the presence of components capable of providing a detectable signal in response to drug metabolization, with a compound to be screened under conditions to permit CYP3A4 or CYP3A7 mediated drug metabolization, and (b) detecting the presence or absence of a signal or increase of a signal generated from the metabolized drug, wherein the presence or increase of the signal is indicative for a putative inhibitor.

The term "compound" in a method of the invention includes a single substance or a plurality of substances which may or may not be identical.

Said compound(s) may be chemically synthesized or produced via microbial fermentation but can also be comprised in, for example, samples, e.g., cell extracts from, e.g., plants, animals or microorganisms. Furthermore, said compounds may be known in the art but hitherto not known to be useful as an inhibitor, respectively. The plurality of compounds may be, e.g., added to the culture medium or injected into a cell or non-human animal of the invention.

If a sample containing (a) compound(s) is identified in the method of the invention, then it is either possible to isolate the compound from the original sample identified as containing the compound, in question or one can further subdivide the original sample, for example, if it consists of a plurality of different compounds, so as to reduce the number of different substances per sample and repeat the method with the subdivisions of the original sample. It can then be determined whether said sample or compound displays the desired properties, for example, by the methods described herein or in the literature (e.g. (13) and Lehmann, J Clin Invest 102 (1998), 1016-23). Depending on the complexity of the samples, the steps described above can be performed several times, preferably until the sample identified according to the method of the invention only comprises a limited number of or only one substance(s). Preferably said sample comprises substances of similar chemical and/or physical properties, and most preferably said substances are identical. The methods of the present invention can be easily performed and designed by the person skilled in the art, for example in accordance with other cell based assays described in the prior art or by using and modifying the methods as described herein. Furthermore, the person skilled in the art will readily recognize which further compounds and/or enzymes may be used in order to perform the methods of the invention, for example, enzymes, if necessary, that convert a certain compound into the precursor which in turn represents a substrate for the CYP3A4 or CYP3A7 protein. Such adaptation of the method of the invention is well within the skill of the person skilled in the art and can be performed without undue experimentation.

Suitable assays which can be employed in accordance with the present invention are described, for example, in Hashimoto, Eur J Biochem 218 (1993), 585-95 wherein transfection assays with chimeric CYP3A4 genes in HepG2 cells are described. Similarly, the variant CYP3A4 and/or CYP3A7 genes can be expressed or co-expressed in HepG2 cells and analyzed for their transcriptional activity and catalytic properties of CYP3A4 or CYP3A7. Such an assay can also be used for studying the catalytic properties of the CYP3A4 and CYP3A7 on its substrates such as steroids (testosterone, progesterone, androstenedione, cortisol, 17β-oestradiol, 17α-ethynyloestradiol), antibiotics (erythromycin), immunosuppressive (cyclosporine A), benzodiazepine (midazolam), benzothiazepine derivatives (diltiazem, triazolam), and nifedipine. In particular, such tests are useful to add in predicting whether a given drug will interact in an individual carrying the respective variant CYP3A4 and/or CYP3A7 gene. A suitable expression system which can be employed in accordance with above described methods of the present invention is also described in (22). In addition heterologous expression systems such as yeast can be used in order to study the stability, binding properties and catalytic activities of the gene products of the variant CYP3A4 and CYP3A7 genes compared to the corresponding wild type gene product. As mentioned before, the molecular variant CYP3A4 and CYP3A7 genes and their gene products, particularly when employed in the above described methods, can be used for pharmacological and toxicological studies of the metabolism of drugs. Preferred drugs to be tested in accordance with the methods of the present invention comprise those described above and include, but are not limited to nifedipine, erythromycin, troleandomycin, quinidine, cyclosporin A, 17 α-ethynylestradiol, lidocaine, diltiazem, dexamethasone, RU486, see also supra. Compounds which can be used in accordance with the present invention include peptides, proteins, nucleic acids, antibodies, small organic compounds, ligands, peptidomimetics, PNAs and the like. Said compounds can also be functional derivatives or analogues of known drugs such as from those described above. Methods for the preparation of chemical derivatives and analogues are well known to those skilled in the art and are described in, for example, Beilstein, Handbook of Organic Chemistry, Springer edition New York Inc., 175 Fifth Avenue, New York, N.Y. 10010 U.S.A. and Organic Synthesis, Wiley, New York, USA. Furthermore, said derivatives and analogues can be tested for their effects according to methods known in the art or as described. Furthermore, peptide mimetics and/or computer aided design of appropriate drug derivatives and analogues can be used, for example, according to the methods described below. Such analogs comprise molecules having as the basis structure of known CYP3A4 and CYP3A7-substrates and/or inhibitors and/or modulators; see infra.

Appropriate computer programs can be used for the identification of interactive sites of a putative inhibitor and the CYP3A4 or CYP3A7 protein of the invention by computer assistant searches for complementary structural motifs (Fassina, Immunomethods 5 (1994), 114-120). Further appropriate computer systems for the computer aided design of protein and peptides are described in the prior art, for example, in Berry, Biochem. Soc. Trans. 22 (1994), 1033-1036; Wodak, Ann. N.Y. Acad. Sci. 501 (1987), 1-13; Pabo, Biochemistry 25 (1986), 5987-5991. The results obtained from the above-described computer analysis can be used in combination with the method of the invention for, e.g., optimizing known inhibitors. Appropriate peptidomimetics and other inhibitors can also be identified by the synthesis of peptidomimetic combinatorial libraries through successive chemical modification and testing the resulting compounds, e.g., according to the methods described herein. Methods for the generation and use of peptidomimetic combinatorial libraries are described in the prior art, for example in Ostresh, Methods in Enzymology 267 (1996), 220-234 and Dorner, Bioorg. Med. Chem. 4 (1996), 709-715. Furthermore, the three-dimensional and/or crystallographic structure of inhibitors and the CYP3A4 or CYP3A7 protein of the invention can be used for the design of peptidomimetic drugs (Rose, Biochemistry 35 (1996), 12933-12944; Rutenberg, Bioorg. Med. Chem. 4 (1996), 1545-1558).

In summary, the present invention provides methods for identifying and obtaining compounds which can be used in specific doses for the treatment of specific forms of diseases, e.g., cancer the chemotherapy of which is complicated by malfunctions of the CYP3A4 or CYP3A7 gene often resulting in an altered activity or level of drug metabolization or sensitive phenotype.

In a preferred embodiment of the method of the invention said cell is a cell of or, obtained by the method of the invention or is comprised in the above-described transgenic non-human animal.

In a further embodiment the present invention relates to a method of identifying and obtaining an CYP3A4 or CYP3A7 inhibitor capable of modulating the activity of a molecular variant of the CYP3A4 or CYP3A7 gene or its gene product comprising the steps of (a) contacting the variant CYP3A4 or CYP3A7 protein of the invention with a first molecule known to be bound by CYP3A4 or CYP3A7 protein to form a first complex of said protein and said first molecule;

(b) contacting said first complex with a compound to be screened; and (c) measuring whether said compound displaces said first molecule from said first complex.

Advantageously, in said method said measuring step comprises measuring the formation of a second complex of said protein and said inhibitor candidate. Preferably, said measuring step comprises measuring the amount of said first molecule that is not bound to said protein.

In a particularly preferred embodiment of the above-described method of said first molecule is nifedipine, rifampicine or corticosterone. Furthermore, it is preferred that in the method of the invention said first molecule is labeled, e.g., with a radioactive or fluorescent label.

In a still further embodiment the present invention relates to a method of diagnosing a disorder related to the presence of a molecular variant CYP3A4 or CYP3A7 gene or susceptibility to such a disorder comprising (a) determining the presence of a polynucleotide of the invention in a sample from a subject; and/or
(b) determining the presence of a variant form of CYP3A4 or CYP3A7 protein, for example, with the antibody of the invention.

In accordance with this embodiment of the present invention, the method of testing the status of a disorder or susceptibility to such a disorder can be effected by using a polynucleotide or a nucleic acid molecule of the invention, e.g., in the form of a Southern or Northern blot or in situ analysis. Said nucleic acid sequence may hybridize to a coding region of either of the genes or to a non-coding region, e.g. intron. In the case that a complementary sequence is employed in the method of the invention, said nucleic acid molecule can again be used in Northern blots. Additionally, said testing can be done in conjunction with an actual blocking, e.g., of the transcription of the gene and thus is expected to have therapeutic relevance. Furthermore, a primer or oligonucleotide can also be used for hybridizing to one of the above-mentioned CYP3A4 or CYP3A7 genes or corresponding mRNAs. The nucleic acids used for hybridization can, of course, be conveniently labeled by incorporating or attaching, e.g., a radioactive or other marker. Such markers are well known in the art. The labeling of said nucleic acid molecules can be effected by conventional methods.

Additionally, the presence or expression of variant CYP3A4 and CYP3A7 genes can be monitored by using a primer pair that specifically hybridizes to either of the corresponding nucleic acid sequences and by carrying out a PCR reaction according to standard procedures. Specific hybridization of the above mentioned probes or primers preferably occurs at stringent hybridization conditions. The term "stringent hybridization conditions" is well known in the art; see, for example, Sambrook et al., "Molecular Cloning, A Laboratory Manual" second ed., CSH Press, Cold Spring Harbor, 1989; "Nucleic Acid Hybridisation, A Practical Approach", Hames and Higgins eds., IRL Press, Oxford, 1985. Furthermore, the mRNA, cRNA, cDNA or genomic. DNA obtained from the subject may be sequenced to identify mutations which may be characteristic fingerprints of mutations in the CYP3A4 and CYP3A7 gene. The present invention further comprises methods wherein such a fingerprint may be generated by RFLPs of DNA or RNA obtained from the subject, optionally the DNA or RNA may be amplified prior to analysis, the methods of which are well known in the art. RNA fingerprints may be performed by, for example, digesting an RNA sample obtained from the subject with a suitable RNA-Enzyme, for example RNase $T_1$, RNase $T_2$ or the like or a ribozyme and, for example, electrophoretically separating and detecting the RNA fragments as described above.

Further modifications of the above-mentioned embodiment of the invention can be easily devised by the person skilled in the art, without any undue experimentation from this disclosure; see, e.g., the examples. An additional embodiment of the present invention relates to a method wherein said determination is effected by employing an antibody of the invention or fragment thereof. The antibody used in the method of the invention may be labeled with detectable tags such as a histidine flags or a biotin molecule.

In a preferred embodiment of the present invention, the above described methods comprise PCR, ligase chain reaction, restriction digestion, direct sequencing, nucleic acid amplification techniques, hybridization techniques or immunoassays (Sambrook et al., loc. cit. CSH cloning, Harlow and Lane loc. cit. CSH antibodies).

In a preferred embodiment of the method of the present invention said disorder is cancer.

In a further embodiment of the above-described method, a further step comprising administering to the subject a medicament to abolish or alleviate said variations in the CYP3A4 or CYP3A7 gene in accordance with all applications of the method of the invention allows treatment of a given disease before the onset of clinical symptoms due to the phenotype response caused by the CYP3A4 or CYP3A7 gene.

In a preferred embodiment of the method of the invention said medicament are chemotherapeutic agents such as substrates of CYP3A4: paclitaxen (Eur J Drug Metab Pharmacokinet 23 (1998), 417-24), tamoxifen and toremifene (Drug Metab Dispos 27 (1999), 681-8; Clin Pharmacol Ther 64 (1998), 648-54; Clin Pharmacol Ther 57 (1995), 628-35), trofosfamide (Cancer Chemother Pharmacol 44 (1999), 327-334), cyclophosphamide and ifosfamide (Drug Metab Dispos 27 (1999), 655-66; Cancer Res 58 (1998), 4391-401; Br J Clin Pharmacol 40 (1995), 523-30), taxotere (Pharmacogenetics 8 (1998), 391-401; Clarke, Clin Pharmacokinet 36 (1999), 99-114).

In another preferred embodiment of the above-described methods, said method further comprises introducing
(i) a functional and expressible wild type CYP3A4 or CYP3A7 gene or
(ii) a nucleotide acid molecule or vector of the invention into cells.

In this context and as used throughout this specification, "functional" CYP3A4 and CYP3A7 gene means a gene wherein the encoded protein having part or all of the primary structural conformation of the wild type CYP3A4 and CYP3A7 protein, i.e. possessing the biological property of metabolizing drugs and controlling the CYP3A4, CYP3A7 gene, respectively. This embodiment of the present invention is suited for therapy of cancer in particular in humans. Detection of the expression of a variant CYP3A4 and/or CYP3A7 gene would allow the conclusion that said expression is interrelated to the generation or maintenance of a corresponding phenotype of the disease. Accordingly, a step would be applied to reduce the expression level to low levels or abolish the same. This can be done, for example, by at least partial elimination of the expression of the mutant gene by biological means, for example, by the use of ribozymes, antisense nucleic acid molecules, intracellular antibodies or the above described inhibitors against the variant forms of these CYP3A4 and/or CYP3A7 proteins. Furthermore, pharmaceutical products may be developed that reduce the expression levels of the corresponding mutant proteins and genes.

In a further embodiment the invention relates to a method for the production of a pharmaceutical composition comprising the steps of any one of the above described methods and synthesizing and/or formulating the compound identified in step (b) or a derivative or homologue thereof in a pharmaceutically acceptable form. The therapeutically useful compounds identified according to the method of the invention may be formulated and administered to a patient as discussed above. For uses and therapeutic doses determined to be appropriate by one skilled in the art see infra.

Furthermore, the present invention relates to a method for the preparation of a pharmaceutical composition comprising the steps of the above-described methods; and formulating a drug or pro-drug in the form suitable for therapeutic application and preventing or ameliorating the disorder of the subject diagnosed in the method of the invention.

Drugs or pro-drugs after their in vivo administration are metabolized in order to be eliminated either by excretion or by metabolism to one or more active or inactive metabolites (Meyer, J. Pharmacokinet. Biopharm. 24 (1996), 449-459). Thus, rather than using the actual compound or inhibitor identified and obtained in accordance with the methods of the present invention a corresponding formulation as a pro-drug can be used which is converted into its active in the patient. Precautionary measures that may be taken for the application of pro-drugs and drugs are described in the literature; see, for review, Ozama, J. Toxicol. Sci. 21 (1996), 323-329).

In a preferred embodiment of the method of the present invention said drug or prodrug is a derivative of a medicament as defined hereinbefore.

In a still further embodiment the present invention relates to an inhibitor identified or obtained by the method described hereinbefore. Preferably, the inhibitor binds specifically to the variant CYP3A4 or CYP3A7 protein of the invention. The antibodies, nucleic acid molecules and inhibitors of the present invention preferably have a specificity at least substantially identical to binding specificity of the natural ligand or binding partner of the CYP3A4 or CYP3A7 protein of the invention. An antibody or inhibitor can have a binding affinity to the CYP3A4 or CYP3A7 protein of the invention of at least $10^5$ M$^{-1}$, preferably higher than $10^7$ M$^{-1}$ and advantageously up to $10^{10}$ M$^{-1}$ in case CYP3A4 or CYP3A7 activity should be repressed. Hence, in a preferred embodiment, a suppressive antibody or inhibitor of the invention has an affinity of at least about $10^{-7}$ M, preferably at least about $10^{-9}$ M and most preferably at last about $10^{-11}$ M.

Furthermore, the present invention relates to the use of an oligo- or polynucleotide for the detection of a polynucleotide of the invention and/or for genotyping of corresponding individual CYP3A4 or CYP3A7 alleles. Preferably, said oligo- or polynucleotide is a polynucleotide or a nucleic acid molecule of the invention described before.

In a particular preferred embodiment said oligonucleotide is about 15 to 50, preferably 20 to 40, more preferably 20 to 30 nucleotides in length and comprises the nucleotide sequence of any one of SEQ ID NOS: 1 to 127, 140, 141 or 142 or a complementary sequence.

Hence, in a still further embodiment, the present invention relates to a primer or probe consisting of an oligonucleotide as defined above. In this context, the term "consisting of" means that the nucleotide sequence described above and employed for the primer or probe of the invention does not have any further nucleotide sequences of the CYP3A4 or CYP3A7 gene immediately adjacent at its 5' and/or 3' end. However, other moieties such as labels, e.g., biotin molecules, histidin flags, antibody fragments, colloidal gold, etc. as well as nucleotide sequences which do not correspond to the CYP3A4 or CYP3A7 gene may be present in the primer and probes of the present invention. Furthermore, it is also possible to use the above described particular nucleotide sequences and to combine them with other nucleotide sequences derived from the CYP3A4 or CYP3A7 gene wherein these additional nucleotide sequences are interspersed with moieties other than nucleic acids or wherein the nucleic acid does not correspond to nucleotide sequences of the CYP3A4 or CYP3A7 gene. Furthermore, it is evident to the person skilled in the art that the oligonucleotide can be modified, for example, by thio-phosphate-backbones and/or base analogs well known in the art (Flanagan, Proc. Natl. Acad. Sci. USA 96 (1999), 3513-8; Witters, Breast Cancer Res. Treat. 53 (1999), 41-50; Hawley, Antisense Nucleic Acid Drug Dev. 9 (1999), 61-9; Peng Ho, Brain Res. Mol. Brain Res. 62 (1998), 1-11; Spiller, Antisense Nucleic Acid Drug Dev. 8 (1998), 281-93; Zhang, J. Pharmacol. Exp. Ther. 278 (1996), 971-9; Shoji, Antimicrob. Agents Chemother. 40 (1996), 1670-5; Crooke, J. Pharmacol. Exp. Ther. 277 (1996), 923-37).

In addition, the present invention relates to the use of an antibody or a substance capable of binding specifically to the gene product of an CYP3A4 or CYP3A7 gene for the detection of the variant CYP3A4 or CYP3A7 protein of the invention, the expression of a molecular variant CYP3A4 or CYP3A7 gene comprising a polynucleotide of the invention and/or for distinguishing CYP3A4 and CYP3A7 alleles comprising a polynucleotide of the invention.

Moreover, the present invention relates to a composition, preferably pharmaceutical composition comprising the antibody, the nucleic acid molecule, the vector or the inhibitor of the present invention, and optionally a pharmaceutically acceptable carrier. These pharmaceutical compositions comprising, e.g., the inhibitor or pharmaceutically acceptable salts thereof may conveniently be administered by any of the routes conventionally used for drug administration, for instance, orally, topically, parenterally or by inhalation. Acceptable salts comprise acetate, methylester, HCl, sulfate, chloride and the like. The compounds may be administered in conventional dosage forms prepared by combining the drugs with standard pharmaceutical carriers according to conventional procedures. These procedures may involve mixing, granulating and compressing or dissolving the ingredients as appropriate to the desired preparation. It will be appreciated that the form and character of the pharmaceutically acceptable character or diluent is dictated by the amount of active ingredient with which it is to be combined, the route of administration and other well-known variables. The carrier(s) must be "acceptable" in the sense of being compatible with the other ingredients of the formulation and not deleterious to the recipient thereof. The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are phosphate buffered saline solution, syrup, oil such as peanut oil and olive oil, water, emulsions, various types of wetting agents, sterile solutions and the like. Similarly, the carrier or diluent may include time delay material well known to the art, such as glyceryl mono-stearate or glyceryl distearate alone or with a wax.

The dosage regimen will be determined by the attending physician and other clinical factors; preferably in accordance with any one of the above described methods. As is well known in the medical arts, dosages for any one patient depends upon many factors, including the patient's size, body surface area, age, the particular compound to be administered, sex, time and route of administration, general health, and other drugs being administered concurrently. Progress can be monitored by periodic assessment.

Furthermore, the use of pharmaceutical compositions which comprise antisense-oligonucleotides which specifically hybridize to RNA encoding mutated versions of a CYP3A4 or CYP3A7 gene according to the invention or which comprise antibodies specifically recognizing mutated CYP3A4 or CYP3A7 protein but not or not substantially the functional wild-type form is conceivable in cases in which the concentration of the mutated form in the cells should be reduced.

Thanks to the present invention the particular drug selection, dosage regimen and corresponding patients to be treated can be determined in accordance with the present invention. The dosing recommendations will be indicated in product labeling by allowing the prescriber to anticipate dose adjustments depending on the considered patient group, with information that avoids prescribing the wrong drug to the wrong patients at the wrong dose.

Furthermore, the present invention relates to a diagnostic composition or kit comprising any one of the afore-described polynucleotides, vectors, host cells, variant CYP3A4 and CYP3A7 proteins, antibodies, inhibitors, nucleic acid molecules or the corresponding vectors of the invention, and optionally suitable means for detection.

The kit of the invention may contain further ingredients such as selection markers and components for selective media suitable for the generation of transgenic cells and animals. The kit of the invention may advantageously be used for carrying out a method of the invention and could be, inter alia, employed in a variety of applications, e.g., in the diagnostic field or as research tool. The parts of the kit of the invention can be packaged individually in vials or in combination in containers or multicontainer units. Manufacture of the kit follows preferably standard procedures which are known to the person skilled in the art. The kit or diagnostic compositions may be used for methods for detecting expression of a mutant form of CYP3A4 or CYP3A7 gene in accordance with any one of the above-described methods of the invention, employing, for example, immunoassay techniques such as radioimmunoassay or enzymeimmunoassay or preferably nucleic acid hybridization and/or amplification techniques such as those described herein before and in the examples.

Some genetic changes lead to altered protein conformational states. For example, some variant CYP3A4 or CYP3A7 proteins may possess a tertiary structure that renders them far less capable of facilitating drug metabolization and transcription initiation, respectively. Restoring the normal or regulated conformation of mutated proteins is the most elegant and specific means to correct these molecular defects, although it is difficult. Pharmacological manipulations thus may aim at restoration of wild-type conformation of the protein. Thus, the polynucleotides and encoded proteins of the present invention may also be used to design and/or identify molecules which are capable of activating the wild-type function of a CYP3A4 or CYP3A7 gene or protein.

In another embodiment the present invention relates to the use of a drug or prodrug for the preparation of a pharmaceutical composition for the treatment or prevention of a disorder diagnosed by the method described hereinbefore.

Furthermore, the present invention relates to the use of an effective dose of a nucleic acid sequence encoding a functional and expressible wild type CYP3A4 or CYP3A7 protein for the preparation of a pharmaceutical composition for treating, preventing and/or delaying a disorder diagnosed by the method of the invention. A gene encoding a functional and expressible CYP3A4 or CYP3A7 protein can be introduced into the cells which in turn produce the protein of interest. Gene therapy, which is based on introducing therapeutic genes into cells by ex-vivo or in-vivo techniques is one of the most important applications of gene transfer. Suitable vectors and methods for in-vitro or in-vivo gene therapy are described in the literature and are known to the person skilled in the art; see, e.g., Giordano, Nature Medicine 2 (1996), 534-539; Schaper, Circ. Res. 79 (1996), 911-919; Anderson, Science 256 (1992), 808-813; Isner, Lancet 348 (1996), 370-374; Muhlhauser, Circ. Res. 77 (1995), 1077-1086; Wang, Nature Medicine 2 (1996), 714-716; WO94/29469; WO 97/00957 or Schaper, Current Opinion in Biotechnology 7 (1996), 635-640, and references cited therein. The gene may be designed for direct introduction or for introduction via liposomes, or viral vectors (e.g. adenoviral, retroviral) into the cell. Preferably, said cell is a germ line cell, embryonic cell, or egg cell or derived therefrom, most preferably said cell is a stem cell.

As is evident from the above, it is preferred that in the use of the invention the nucleic acid sequence is operatively linked to regulatory elements allowing for the expression and/or targeting of the CYP3A4 or CYP3A7 protein to specific cells. Suitable gene delivery systems that can be employed in accordance with the invention may include liposomes, receptor-mediated delivery systems, naked DNA, and viral vectors such as herpes viruses, retroviruses, adenoviruses, and adeno-associated viruses, among others. Delivery of nucleic acids to a specific site in the body for gene therapy may also be accomplished using a biolistic delivery system, such as that described by Williams (Proc. Natl. Acad. Sci. USA 88 (1991), 2726-2729). Standard methods for transfecting cells with recombinant DNA are well known to those skilled in the art of molecular biology, see, e.g., WO 94/29469; see also supra. Gene therapy may be carried out by directly administering the recombinant DNA molecule or vector of the invention to a patient or by transfecting cells with the polynucleotide or vector of the invention ex vivo and infusing the transfected cells into the patient.

In a preferred embodiment of the uses and methods of the invention, said disorder is cancer.

These and other embodiments are disclosed or are obvious from and encompassed by the description and examples of the present invention. Further literature concerning any one of the methods, uses and compounds to be employed in accordance with the present invention may be retrieved from public libraries, using for example electronic devices. For example the public database "Medline" may be utilized which is available on the Internet, e.g. the PubMed website, the NCBI website, the InfoBiogen website, the Institute for Genomic Research (TIGR) website, and the lycos website. An overview of patent information in biotechnology and a survey of relevant sources of patent information useful for retrospective searching and for current awareness is given in Berks, TIBTECH 12 (1994), 352-364.

The pharmaceutical and diagnostic compositions, uses, methods of the invention can be used for the diagnosis and treatment of all kinds of diseases hitherto unknown as being related to or dependent on variant CYP3A4 and CYP3A7 genes. The compositions, methods and uses of the present invention may be desirably employed in humans, although animal treatment is also encompassed by the methods and uses described herein.

BRIEF DESCRIPTION OF THE FIGURES

FIG. 4: Examples of polymorphisms in the CYP3A4 and CYP3A7 genes. Numbering of polymorphic sites within the exons of CYP3A4 is based on the GenBank sequence M14096. Numbering of polymorphic sites within the exons of CYP3A7 is based on the GenBank sequence gi4503232.

FIG. 6: Genomic sequences and polymorphisms in CYP3A4 and CYP3A7 genes. Primers used for the amplification and sequencing (Table 1), as well as splice sites are underlined. Thick underlined are polymorphic sites and they are shown as the wild-type and variant base, separated by an arrow.

Figure 1:
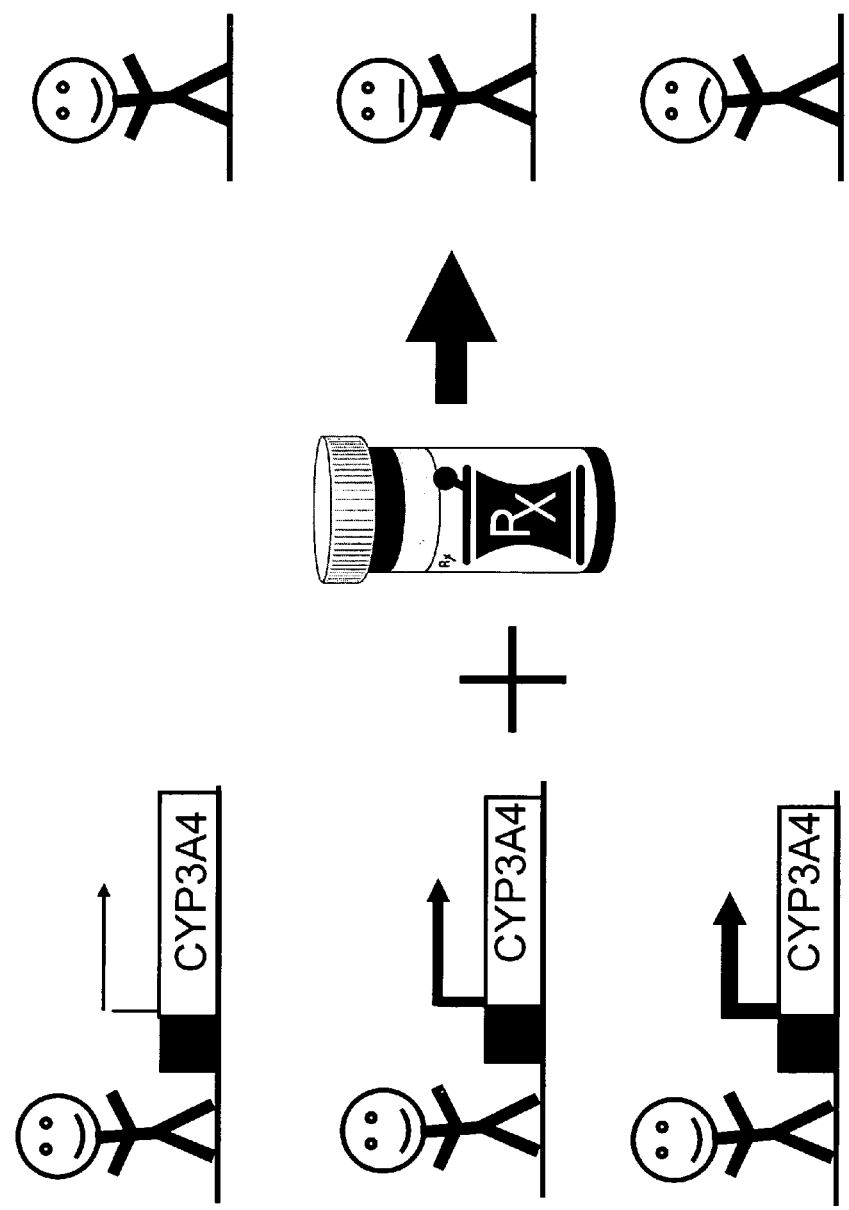
FIG. 1: Differences in the genetic makeup influence the efficacy and safety of drug treatment.
Figure 2:
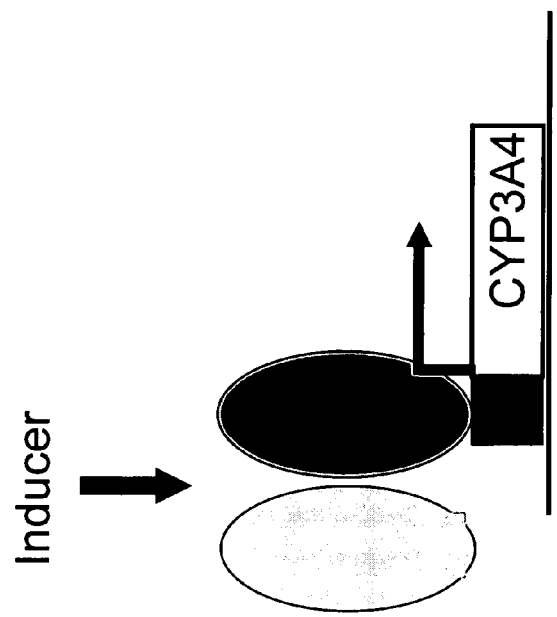
FIG. 2: A current model of the regulation of CYP3A4 by hPXR.
Figure 3:
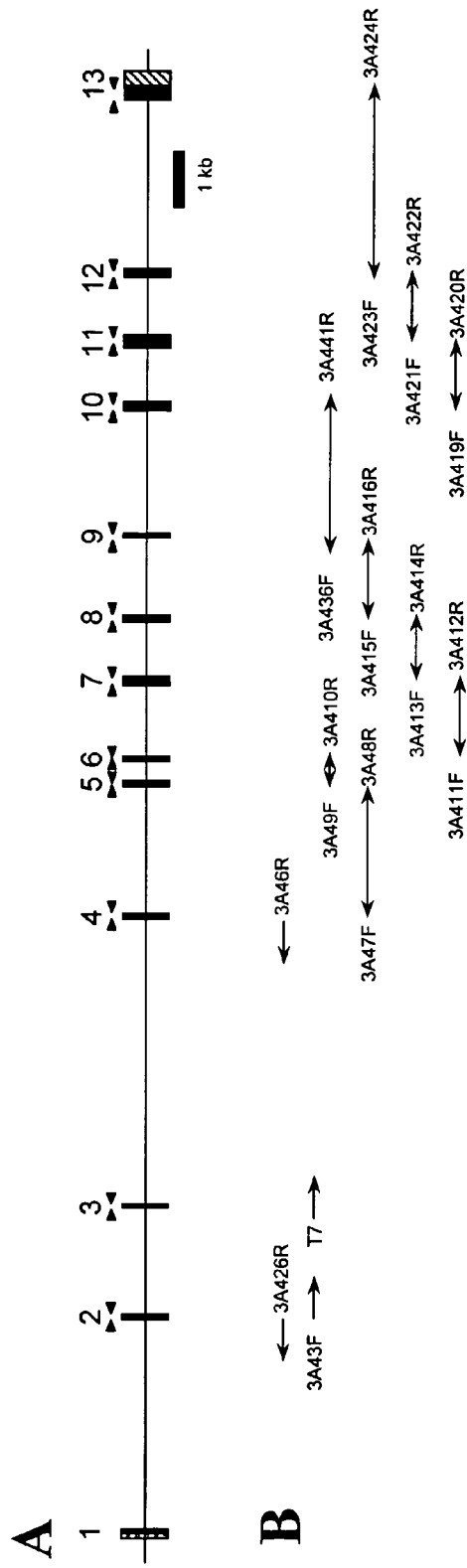
FIG. 3: (A) Structure of the CYP3A4 gene as described in Ref. by Hashimoto, Eur Biochem 218 (1993) 585-95 and confirmed in this study. Coding regions are indicated as filled rectangles, the non-coding 5' untranslated region as a dashed rectangle. Arrowheads represent the positions of oligonucleotides used to screen the coding region of the gene (see Table 2 for the oligonucleotide sequences). (B) Determination of the exon flanking sequences. Double-headed arrows indicate genomic regions amplified by PCR. Single-headed arrows indicate sequences obtained by direct sequencing of BAC clones. The sequences of oligonucleotides shown in (B) are given in Table 1.

The invention will now be described by reference to the following examples which are merely illustrative and are not to be construed as a limitation of the scope of the present invention.

EXAMPLES

Example 1

Genomic Organization and Oligonucleotides for the Amplification of the Coding Regions of CYP3A4 and CYP3A7

The genomic structure of CYP3A4 has been described in an earlier work (Hashimoto, Eur. J. Biochem. 218 (1993), 585-95); however, the published exon flanking sequences were too short to design oligonucleotides for exon amplification. In accordance with the present invention the sequences surrounding the CYP3A4 exons 5, 7, 9, 12 and 13 have been elucidated by sequencing of PCR (Polymerase Chain Reaction)-amplified fragments containing parts of two neighboring exons and the intercalated intron. The sequences surrounding the CYP3A4 exons 6, 8, 10 and 11 have been elucidated by sequencing of PCR-amplified fragments containing parts of two neighboring exons and the intercalated intron as well as by sequencing the 3A4-containing bacterial artificial chromosome (BAC) (GenBank Accession Number AF280107). The sequences surrounding the CYP3A4 exons 1, 3 and 4 were derived from a CYP3A4-containing bacterial artificial chromosome (BAC) (GenBank Accession Number AF280107). Oligonucleotides used for the amplification of these fragments and for sequencing of the BAC were derived from a CYP3A4 cDNA sequence (GenBank accession number M14096) upon consideration of the exon/intron organization of the gene (Hashimoto, Eur J Biochem 218 (1993), 585-95). The sequences thus obtained were used to design oligonucleotides for the amplification of exons 1 and 3-13. Oligonucleotides for the amplification of exons 2 were designed using the recently determined sequence of a CYP3A4-containing bacterial artificial chromosome (GenBank Accession Number AF280107)

The sequences thus obtained were used to design oligonucleotides for amplification of the gene exons. Their composition and the sizes of the resulting DNA fragments are given in Table 2. Besides the exon sequences, fragments amplified contain also some flanking intronic sequences, including the splice sites, as well as some 5'- and 3'-UTR (untranslated region) sequences of the gene.

Example 2

Isolation of Genomic DNA, Amplification, Purification and Sequencing of CYP3A4 and CYP3A7 Gene Fragments Genomic DNA was isolated from Caucasian blood or liver samples using Qiagen blood and tissue DNA isolation kits. Samples were collected by the Institute of Clinical Pharmacology, University Medical Center Charite, Humboldt University in Berlin, Germany, by the Dr. Margarete Fischer-Bosch-Institute of Clinical Pharmacology in Stuttgart, Germany, by Department of Pharmacology, Biozentrum, University of Basel, Switzerland, and by Parexel International, Berlin, Germany, under consideration of all necessary ethical and legal requirements. Conditions for the amplification of CYP3A4 and CYP3A7 gene fragments by PCR are given in Table 2, respectively. The complete sequences of the amplicons are given in FIG. 6. The quality of amplicons was routinely checked by agarose gel electrophoresis. The fragments were then processed through PCR purification columns (Qiagen) which remove all the components of the PCR that could otherwise interfere with the subsequent sequencing reaction.

The sequencing reaction was performed using the dye-terminator method and the samples were then resolved on polyacrylamide gels (Perkin-Elmer 377 and 3700 sequencing machines). Both strands were routinely sequenced to assure high accuracy of the results and the detection of heterozygotes. The sequences were visually inspected for their quality and then analyzed for the presence of polymorphisms using the PHRED/PHRAP/POLYPHRED/CONSED software package (University of Washington, Seattle, USA).

Example 3

Polymorphisms in the CYP3A4 and CYP3A7 Gene

In accordance with the present invention, a panel of Caucasian DNA samples were screened for mutations in exons 1 to 13 of the CYP3A4 gene, and in exon 11 of the CYP3A7 gene. The results for CYP3A4 were obtained for between 296 and 426 chromosomes per PCR fragment (Table 3). A comparison of the sequences generated with the three CYP3A4 cDNAs originally published (Beaune, Proc Natl Acad Sci USA 83 (1986), 8064-8; Gonzalez, Dna 7 (1988), 79-86; Bork, J Biol Chem 264 (1989), 910-9) indicates that only the cDNA with a GenBank Accession Number M18907 (Gonzalez, Dna 7 (1988), 79-86) encodes for a CYP3A4 protein such as expressed by most Caucasians. An overview of variants found is given in Table 3. In the CYP3A4 gene, we have identified altogether 18 variant positions, all of which are single nucleotide polymorphisms (SNPs). Ten variants are located within the protein-coding regions of CYP3A4, one within the untranslated region (3' UTR) of exon 13, and seven within the exon-flanking intronic sequences. No variants have been found within the splice sites of the gene's exons. Fifteen out of 18 variants had allelic frequencies below, and three, including one missense mutation (M1), above, 1% (Table 3). The highest allelic frequency (9.5%) exhibits the M14 variant located in intron 10 (Table 3).

Out of 10 variants located in the protein-coding regions of the gene two are silent, whereas eight result in amino acid exchanges of the CYP3A4 protein. Out of the eight missense variants, seven are new, whereas the M8 variant (M445T) is identical to the CYP3A4*3 allele recently described in a Chinese subject (Sata, Clin Pharmacol Ther 67 (2000), 48-56). The most frequent missense mutation (G56D) was found in 2.82% subjects tested (Table 3). Taken together, 7.5% of Caucasians tested in the screen were heterozygous for a variant CYP3A4 protein.

For CYP3A7 a C1229G SNP in exon 11 was found in 17 out of 232 chromosomes screened. The SNP results in a non-conservative amino acid exchange (Thr→Arg) at position 409 of the CYP3A7 protein.

Example 4

An Enzymatic Test for the CYP3A7 Exon 11 C1229G Polymorphism

Figure 5:
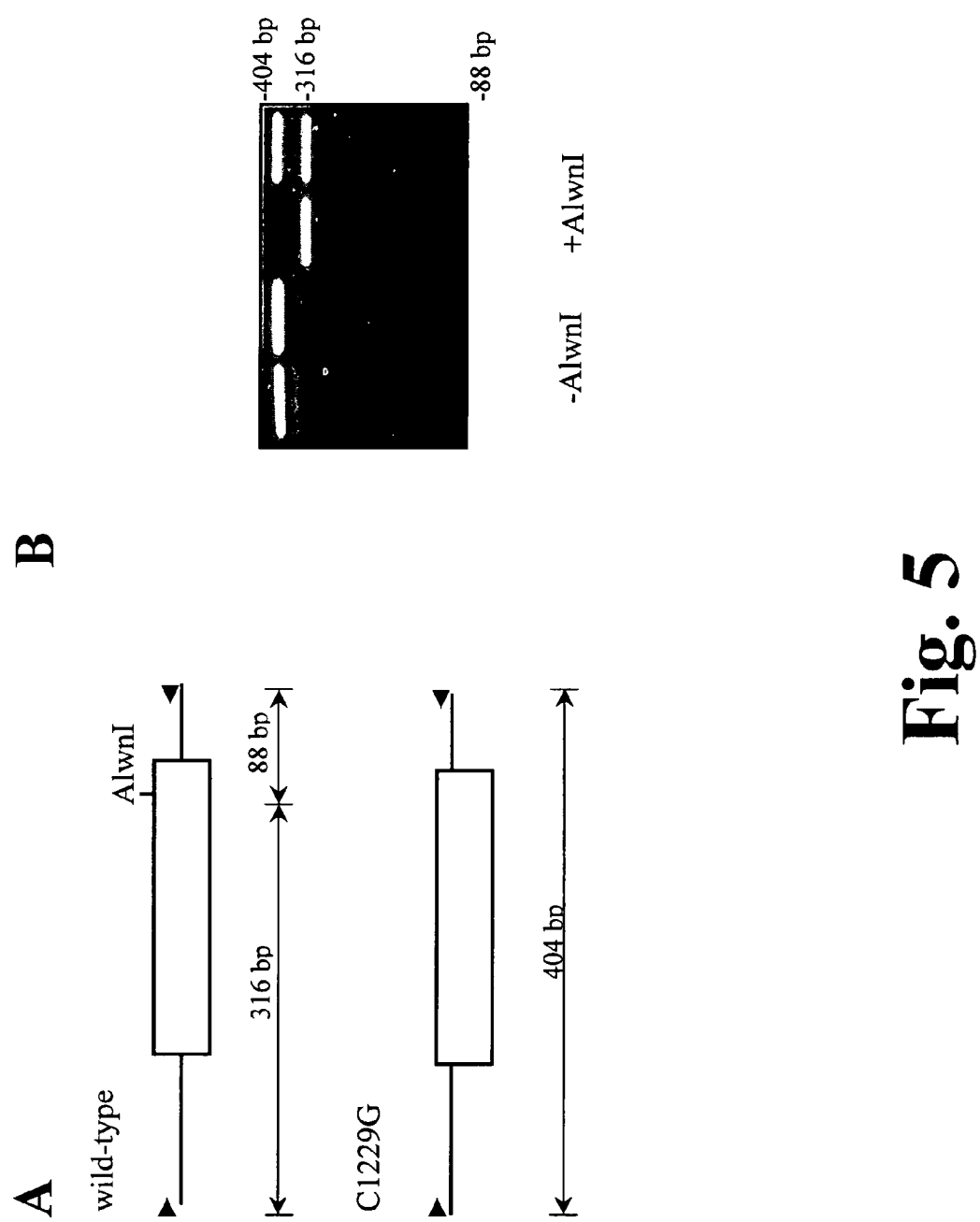
FIG. 5: An enzymatic test for the CYP3A7 exon 11 C1229G (Thr409Arg) polymorphism. (A) The mutation eliminates the unique AlwnI restriction site from the exon 11-containing fragment amplified with oligonucleotides 3A442F and 3A438R (arrowheads). (B) Genotyping of a wild-type (wt/wt) and a heterozygous (wt/C1229G) DNA sample by means of the AlwnI restriction digest.

The C1229G polymorphism detected in exon 11 of CYP3A7 results in the loss of an Alwnl restriction site (FIG. 5A). In accordance with the present invention an Alwnl-based test was developed for the genotyping of the C1229G allele. An example is shown in FIG. 5B. A digest of the 404 bp genomic fragment amplified from a wild-type sample (wt/wt) with primers 3A742F and 3A738R (Table 2) generates two fragments of 316 bp and 88 bp, respectively. In a heterozygous sample (wt/C1229G), approximately half of the DNA remains undigested, due to the loss of the restriction site in the mutant allele.

Because population genetics enables a calculation of the expected frequency of homozygous vs. heterozygous alleles of a defined gene (Hardy Weinberg formula, $p\ e2+2pq+q\ e2=1$), it is also possible to confirm the predicted (with that formula) distribution of homozygous vs. heterozygous alleles and deviations with the experimental findings. This can serve as internal control and confirmation that a detected sequence deviation indeed represents a novel allele.

Example 5

CYP3A4 Mutant Expression, Purification and Western Blotting

Mutants were expressed in *E. coli* TOPP3 cells. Cultures of each strain were started from single colonies in 2-ml of LB media containing ampicillin (50 µg/ml) and tetracycline (15 µg/ml) and grown overnight at 37° C. with shaking. Larger, 20-ml cultures of each sample were inoculated and grown as described for the 2-ml cultures. Starter cultures (15 ml) were inoculated into 250-ml of TB media containing ampicillin (50 µg/ml) and grown 2-3 hr at 37° C. at 250 rpm. δ-aminolevulinic acid (80 mg/L) and IPTG (1 mM) were added and the cultures grown 72 hr at 30° C. at 190 rpm. The cells were harvested, sonicated and CHAPS solubilized, and the protein was purified on Talon Metal Affinity resin from Clontech (Palo Alto, Calif.). Final P450 content was measured by reduced CO difference spectra (Omura, J Biol Chem 239 (1964), 2370-2378), and each protein was visualized on an 8.5% SDS PAGE gel stained with Coomassie blue. Western Blot analysis of CYP3A4 wild-type, M2, M5 and M7 was performed by resolving 1 pmol of 3A4 wildtype and M5, and 8 µl of M2 and M7 total protein sample on an 8.5% SDS PAGE gel. The samples were then transferred to nitrocellulose and probed with an anti-3A12 polyclonal antibody known to cross-react with CYP3A4 (Ciaccio, Arch Biochem Biophys 271 (1989), 284-99).

Example 6

Functional Characterization of CYP3A4 Protein Variants

Figure 7:
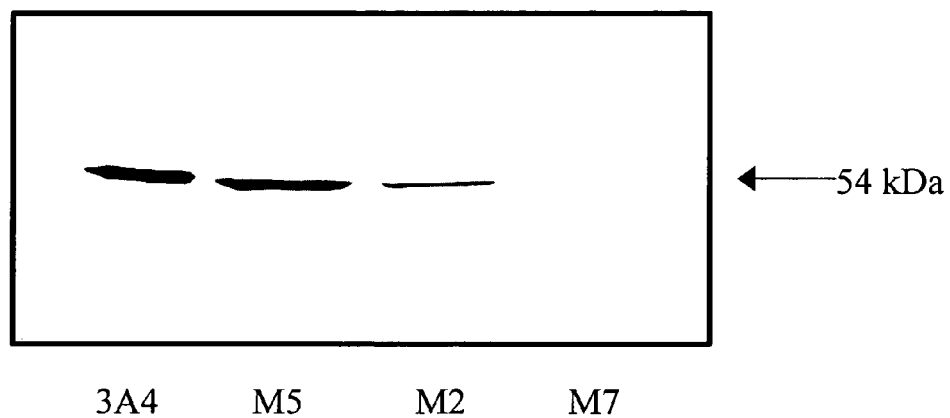
FIG. 7: Immunoblot of wild-type CYP3A4 (3A4), R130Q (M2), T363M (M5), and P416L (M7). P450 (1 pmol) was loaded into each lane, transferred to nitrocellulose, and probed with anti-3A12 IgG as described in Materials and Methods.

The effect of the protein variants on the expression level and catalytical activity of CYP3A4 was investigated using a bacterial CYP3A4 expression system. Sequence variants were introduced into the pSE3A4H expression vector (Harlow, J Biol Chem 272 (1997), 5396-402) which encodes for a CYP3A4 protein identical to that found in most Caucasians. No other, unwanted mutations were introduced into the CYP3A4 insert or the promoter driving its expression as confirmed by sequencing. Mutants M1-M8 were expressed in *E. coli* as described in Example 5, the expression of the CYP3A4 holoenzyme assessed by measuring reduced CO difference spectra, and the protein purified. All but M2, M5 and M7 mutants were detectable at levels similar to CYP3A4. M5 expressed at levels less than 10% of CYP3A4 and demonstrated some instability, as indicated by inconsistency of P450 measurements in multiple determinations. M2 and M7 resulted in no detectable P450 holoprotein in four attempts. The expression of M2, M5, and M7 was further investigated by Western Blotting using an anti-CYP3A12 polyclonal antibody known to cross-react with CYP3A4 (Ciaccio, Arch Biochem Biophys 271 (1989), 284-99) as described in Example 5. Bands of the expected size (about 54 kDA) were visualized in the lanes containing CYP3A4 wild-type and M2 mutant proteins (FIG. 7). Only a very faint band was seen in the lane containing M7, and this band was not significantly darker than background. These results indicate that M2 and M7 mutations abolish, whereas M5 diminishes the expression of CYP3A4 holoenzyme.

Following the reconstitution with NADPH-cytochrome P450 reductase and cytochrome $b_5$, the catalytical activities of M1, M4, M5 and M6 variants were measured using testosterone, progesterone and 7-BFC as substrates (Tables 5-7). Mutants M1 and M4 displayed steroid hydroxylase activities and 7-BFC debenzylase activity that differed from CYP3A4 (Tables 5-7). M4 displayed <50% of wild-type CYP3A4 steroid hydroxylase activity at the lower steroid concentration (Tables 5 and 6), and <50% of CYP3A4 7-BFC debenzylase activity (Table 7). M1 showed 137% of CYP3A4 7-BFC debenzylase activity (Table 7) but only 53% of the CYP3A4 testosterone hydroxylase activity at a testosterone concentration of 25 µM (Table 5). Neither M1 nor M4 mutant displayed alterations in their steroid hydroxylase metabolite profiles when compared with wild-type CYP3A4. The activity of the M5 mutant was approximately half that of wild-type protein (Table 5-7), although this finding could in part reflect M5's apparent reduced stability. On the other hand, mutant M6 displayed a strikingly altered testosterone hydroxylase metabolite profile (Table 5).

TABLE 1

Oligonucleotides used to determine the exon/intron boundaries of the CYP3A4 gene and of the exon 11 of CYP3A7 (in bold).

| Name | Position | Sequence (5'-3') | Sequence Identifier |
|---|---|---|---|
| T7 | BAC CS | TAATACGACTCACTATAGGG | SEQ ID NO:1 |
| 3A43F | exon 2 | GAACCCATTCACATGGAC | SEQ ID NO:2 |
| 3A46R | exon 4 | TGATCATGTCAGGATCTG | SEQ ID NO:3 |
| 3A47F | exon 4 | GGTCAACAGCCTGTGCTG | SEQ ID NO:4 |
| 3A48R | exon 5 | TCCACTGGTGAAGGTTGG | SEQ ID NO:5 |
| 3A49F | exon 5 | GTGCCATCTCTATAGCTG | SEQ ID NO:6 |
| 3A410R | exon 6 | CTTCCCGCCTCAGATTTC | SEQ ID NO:7 |
| 3A411F | exon 6 | GAAATCTGAGGCGGGAAG | SEQ ID NO:8 |
| 3A412R | exon 7 | GGGTCTTGTGGATTGTTG | SEQ ID NO:9 |
| 3A413F | exon 7 | CAACAATCCACAAGACCC | SEQ ID NO:10 |
| 3A414R | exon 8 | GTGTATCTTCGAGGCGAC | SEQ ID NO:11 |
| 3A415F | exon 8 | CTTTCCATTCCTCATCCC | SEQ ID NO:12 |
| 3A416R | exon 9 | CCTTTGTGGGACTCAGTTTC | SEQ ID NO:13 |
| 3A419F | exon 10 | GCCACTCACCCTGATGTC | SEQ ID NO:14 |
| 3A720R | exon 11 | ATCACCACCCACCCTTTG | SEQ ID NO:15 |
| 3A721F | exon 11 | CAAAGGGTGGGTGGTGAT | SEQ ID NO:16 |
| 3A422R | exon 12 | GAGAGCAAACCTCATGCC | SEQ ID NO:17 |
| 3A423F | exon 12 | GGCATGAGGTTTGCTCTC | SEQ ID NO:18 |
| 3A424R | exon 13 | GGTGCCATCCCTTGACTC | SEQ ID NO:19 |
| 3A426R | exon 2 | GCAGAGGTGTGGGCCCTG | SEQ ID NO:20 |
| 3A4436F | intron 8 | GGAGATCAAGGACCACGCTTGTG | SEQ ID NO:21 |
| 3A441R | intron 10 | CTTACGCTTCTGCCAGTAGCAACC | SEQ ID NO:22 |
| CYP3A4PF | promoter | AACAGGCGTGGAAACACAAT | SEQ ID NO:23 |
| CYP3A4PR | promoter | CTTTCCTGCCCTGCACAG | SEQ ID NO:24 |

Fifty ng of genomic DNA was added to a reaction mix (total volume 30 or 50 μl) containing 1×PCR buffer (Q=Qiagen, Cat. Nr. 1005479, or B2=Boehringer (currently Roche) Expand Long Template PCR Buffer number 2, Cat. Nr. 1742655), 0.25 μM each oligonucleotide (Metabion), 200 μM dNTPs, and 1 U of Taq polymerase (Qiagen). Amplifications were performed on a RoboCycler Gradient 96 (Stratagene) with an initial denaturation step of 2 min. at 94° C. followed by 32 amplification cycles of denaturation (40 sec., 94° C.), annealing (45 sec., temperatures 56-60° C.), and extension (60-150 sec., 72° C.). This was followed by a final extension step 5 min., 72° C. The sequencing of PCR fragments and BAC clones was performed on a GeneAmp PCR System 9700 (Perkin-Elmer) using a dye-terminator DNA sequencing kit (Perkin-Elmer, Cat. Nr. 4303154), according to manufacturers's instructions.

TABLE 2

CYP3A4 (exons 1 to 13) and CYP3A7 (exon 11, bold) polymorphism screen: oligonucleotide sequences, amplification conditions and fragment size

| Exon | Primer name | Primer sequence (5'-3' orientation) | Location on BAC 22300 | Fragment length | Annealing Temp. | SEQ ID NO: |
|---|---|---|---|---|---|---|
| 1 | 3°4-62F | AACTGCAGGCAGAGCACAGGT | 61838-61858 | 384 bp | 63° C. | 25 |
|   | 3A4-64R | CCACGCCCGGCCTGAACATCT | 62221-62201 |   |   | 26 |
| 2[a] | 3A4-101F | TAGGATCCAATCATCTCCTAC | 65072-65092 | 463 bp | 62° C. | 27 |
|   | 3A4-68F | GGTGTCTCATGGTGGAGG | 65841-65858 |   |   | 28 |
|   | 3A4-103R | AGAGTTAGCAAGAGAGCCCTT | 66303-66283 |   |   | 29 |
| 3 | 3A4-50F | CCTCTAACTGCCAGCAAGTCTG | 67924-67945 | 249 bp | 58° C. | 30 |
|   | 3A4-51R | GCGCTGAGACTGTCCTCTGTG | 68172-68152 |   |   | 31 |
| 4[b] | 3A4-52F | AGTCTGGCTTCCTGGGTTGGGCTC | 73343-73366 | 293 bp | 58° C. | 32 |
|   | 3A4-37R | GAAGTGGACGTGGAACCTTCCTGGAC | 73635-73610 |   |   | 142 |
|   | 3A4-100R | GGGGACAGGATGAAGTGGACG | 73646-73626 | 304 bp | 63° C. | 33 |
| 5 | 3A4-28F | TACAACCATGGAGACCTCC | 75813-75832 | 236 bp | 62° C. | 34 |
|   | 3A4-29R | TACCTGTCCCCACCAGATTC | 76048-76029 |   |   | 35 |
| 6 | 3A4-57F | CCCTTTCCAAGGGGTAGTCC | 76066-76085 | 379 bp | 58° C. | 36 |
|   | 3A4-32R | GTCTGGTCACTGGAATAACCCAACAGCAAGG | 76444-76415 |   |   | 37 |
| 7 | 3A4-33F | GTCTGTCTTGACTGGACATGTGG | 77509-77531 | 393 bp | 58° C. | 38 |
|   | 3A4-34R | GATGATGGTCACACACATATCTTC | 77901-77880 |   |   | 39 |
| 8 | 3A4-35F | GGCTTCCAGTTGAGAACCTTGATGTC | 78723-78748 | 389 bp | 58° C. | 40 |
|   | 3A4-59R | GCTCTAAACATGAGCAGTCTTC | 79111-79090 |   |   | 41 |
| 9 | 3A4-36F | GGAGATCAAGGACCACGCTTGTG | 79584-79606 | 240 bp | 62° C. | 42 |
|   | 3A4-47R | CTCATCATCCTGGAATACTTCCTGC | 79823-79799 |   |   | 43 |
| 10 | 3A4-82F | CCCAGTGTACCTCTGAATTGC | 81959-81979 | 431 bp | 50° C. | 44 |
|   | 3A4-95R | CAGAGCCTTCCTACATAG | 82389-82372 |   |   | 45 |
| 11 | 3A4-97F | CAGTATGAGTTAGTCTCTGG | 83733-83752 | 574 bp | 50° C. | 46 |
|   | 3A4-80R | CATAACTGATGACCTTCATCG | 84306-84286 |   |   | 47 |
| 12 | 3A4-49F | CCTGTGTACTGCTAGTAGAGGG | 85020-85041 | 411 bp | 50° C. | 48 |
|   | 3A4-39R | CACAGATGGGCCTAATTG | 85430-85413 |   |   | 49 |

TABLE 2-continued

CYP3A4 (exons 1 to 13) and CYP3A7 (exon 11, bold) polymorphism
screen: oligonucleotide sequences, amplification conditions and fragment size

| Exon | Primer name | Primer sequence (5'-3' orientation) | Location on BAC 22300 | Fragment length | Annealing Temp. | SEQ ID NO: |
|---|---|---|---|---|---|---|
| 13 | 3A4-48F | GGAGTGTCTCACTCACTFTGATGC | 87799-87822 | 288 bp | 50° C. | 50 |
|  | 3A4-25R | TGGATGAAGCCCATCTTC | 88086-88069 |  |  | 51 |
| 11 | 3A7-42F | CCAGTATGAGTTGTTCTCTGG | 87799-87822 | 404 bp | 58° C. | 140 |
|  | 3A7-38R | AGGCAGAATATGCTTGAACCAGGC | 88086-88069 |  |  | 141 |

[a]Primer 3A4-101F and 3A4-103R are used for amplification of a 1231 bp fragment; primer 3A4-68F and 3A4-103R are used for sequencing
[b]Primers 3A4-52F and 3A4-37R can be used in combination for amplification resulting in a 293 bp fragment at an annealing temperature of 58° C. and primers 3A4-52F and 3A4-100R can be used in combination for amplification resulting in a 304 bp fragment at an annealing temperature of 63° C.

Fifty ng of genomic DNA was added to a reaction mix containing 1×PCR buffer (Qiagen), 0.5 µM oligonucleotides, 200 µM dNTPs, and 1 U of Taq polymerase (Qiagen). Amplifications were performed on a Robocycler Gradient 96 (Stratagene) with an initial denaturation step of 2 min. at 94° C. followed by 32 amplification cycles of denaturation (40 sec., 94° C.), annealing (45 sec., temperatures given above), and extension (60 sec., 72° C.). This was followed by a final extension step 5 min., 72° C. All sequencing reactions were performed on a GeneAmp PCR System 9700 (Perkin-Elmer) using a dye-terminator DNA sequencing kit (Perkin-Elmer, catalog number 4303154), according to manufacturer's instructions.

TABLE 3

Positions, sequences and frequencies of CYP3A4 variants[a]

| Nr | Variant[b] | Nucleotide sequence (5'-3') | Genetic element | Predicted effect | N[c] | Hetero-zygotes found (%) | Homozy-gotes found (%) | Homozy-gotes calcu-lated (%) | Variant allele frequency (%) | SEQ ID NO: (* = reverse complement) |
|---|---|---|---|---|---|---|---|---|---|---|
| M1 | g.6004G>A | TCCCAGGGCTTTTGT .....A........ | Exon 3 | G56D | 426 | 2.82 | 0.00 | 0.0190 | 1.41 | 52 *53 54 *55 |
| M2 | g.13908G>A | ATTACGATCAT .....A..... | Exon 5 | R130Q | 300 | 0.66 | 0.00 | 0.0011 | 0.33 | 60 *61 62 *63 |
| M3 | g.14292G>A | AGCCTGTCACC .....A..... | Exon 6 | V170I | 424 | 0.47 | 0.00 | 0.0006 | 0.24 | 64 *65 66 *67 |
| M4 | g.14304G>C | TGAAACAGTAA .....G..... | Exon 6 | D174H | 424 | 0.47 | 0.00 | 0.0006 | 0.24 | 68 *69 70 *71 |
| M10 | g.14323C>T | GCAGCCATGGG .....T..... | Intron 6 |  | 424 | 0.47 | 0.00 | 0.0006 | 0.24 | 72 *73 74 *75 |
| M11 | g.14329G>T | ATGGGGTTCTG .....T..... | Intron 6 |  | 424 | 0.47 | 0.00 | 0.0006 | 0.24 | 76 *77 78 *79 |
| M12 | g.14357T>G | CCAGCTGCCTG .....G..... | Intron 6 |  | 424 | 1.89 | 0.00 | 0.009 | 0.94 | 80 *81 82 *83 |
| M13 | g.15753T>G | TATCTTTCTCTT ......G....... | Intron 7 |  | 296 | 5.41 | 0.00 | 0.073 | 2.70 | 56 *57 58 *59 |
| M14 | g.20230G>A | GGATGGTACAT .....A..... | Intron 10 |  | 296 | 17.56 | 0.68 | 0.895 | 9.46 | 84 *85 86 *87 |
| M5 | g.21867C>T | TGAAACGCTCA .....T..... | Exon 11 | T363M | 298 | 0.67 | 0.00 | 0.001 | 0.34 | 88 *89 90 *91 |
| M15 | g.21868G>A | GAAACGCTCAG .....A..... | Exon 11 | Silent | 298 | 0.67 | 0.00 | 0.001 | 0.34 | 92 *93 94 *95 |
| M6 | g.21896C>T | TGAGACTTGAC .....T..... | Exon 11 | L373F | 298 | 0.67 | 0.00 | 0.001 | 0.34 | 96 *97 98 *99 |
| M7 | g.22026C>T | CCTCCCTGAAA .....T..... | Exon 11 | P416L | 298 | 0.67 | 0.00 | 0.001 | 0.34 | 100 *101 102 *103 |
| M16 | g.22041C>T | CAAGGCCCCTG .....T..... | Intron 11 |  | 298 | 0.67 | 0.00 | 0.001 | 0.34 | 104 *105 106 *109 |
| M17 | g.23081C>T | ACCAACGTGGA .....T..... | Intron 11 |  | 426 | 0.47 | 0.00 | 0.001 | 0.23 | 108 *107 110 *111 |
| M18 | g.23172T>C | TGGCATGAGGT .....C..... | Exon 12 | M445T | 426 | 0.94 | 0.00 | 0.002 | 0.47 | 112 *113 114 *115 |
| M18 | g.25925C>T | GGCACCGTAAG .....T..... | Exon 13 | Silent | 300 | 0.66 | 0.00 | 0.001 | 0.33 | 116 *112 118 *119 |
| M19 | g.25958T>G | ACTTCTGCTTT .....G..... | 3'UTR |  | 300 | 0.66 | 0.00 | 0.001 | 0.33 | 120 *121 122 *123 |

[a]Variants listed according to their localization along the CYP3A4 gene
[b]Reference sequence GenBank accession number AF280107. The nucleotide A of the first ATG of the CYP3A4 protein has been taken as position 1.
[c]Number of chromosomes screened

TABLE 4

Genetic variants of CYP3A4 and CYP3A7.

| Gene | Position | wt sequence (5'-3') | mut sequence (5'-3') |
|---|---|---|---|
| CYP3A4 | exon 3 | F: TCCCAGGGCTTTTGT | F: TCCCAGGACTTTTGT |
|  |  | R: ACAAAAGCCCTGGGA | R: ACAAAAGTCCTGGGA |
|  | intron 7 | F: TATCTTTCTCTCTT | F: TATCTTGCTCTCTT |
|  |  | R: AAGAGAGAAAGATA | R: AAGAGAGCAAGATA |
|  | exon 5 | F: ATTACGATCAT | F: ATTACAATCAT |
|  |  | R: ATGATCGTAAT | R: ATGATTGTAAT |
|  | exon 6 | F: AGCCTGTCACC | F: AGCCTATCACC |
|  |  | R: GGTGACAGGCT | R: GGTGATAGGCT |
|  | exon 6 | F: TGAAAGAGTAA | F: TGAAACACTAA |
|  |  | R: TTACTCTTTCA | R: TTACTGTTTCA |
|  | intron 6 | F: GCAGCCATGGG | F: GCAGCTATGGG |
|  |  | R: CCCATGGCTGC | R: CCCATAGCTGC |
|  | intron 6 | F: ATGGGGTTCTG | F: ATGGCTTTCTG |
|  |  | R: CAGAACCCCAT | R: CAGAAACCCAT |
|  | intron 6 | F: CCAGCTGCCTG | F: CCACCGGCCTG |
|  |  | R: CAGGCAGCTGG | R: CAGGCCGCTGG |
|  | intron 10 | F: GGATGGTACAT | F: GGATGATACAT |
|  |  | R: ATGTACCATCC | R: ATGTATCATCC |
|  | exon 11 | F: TGAAACGCTCA | F: TGAAATGCTCA |
|  |  | R: TGAGCGTTTCA | R: TGAGCATTTCA |
|  | exon 11 | F: GAAACGCTCAG | F: GAAACACTCAG |
|  |  | R: CTGAGCGTTTC | R: CTGAGTGTTTC |
|  | exon 11 | F: TGAGACTTGAG | F: TGAGATTTGAG |
|  |  | R: CTCAAGTCTCA | R: CTCAAATCTCA |
|  | exon 11 | F: CCTCCCTGAAA | F: CCTCCTTGAAA |
|  |  | R: TTTCAGGGAGG | R: TTTCAAGGAGG |
|  | intron 11 | F: CAAGGCCCCTG | F: CAAGGTCCCTG |
|  |  | R: CAGGGGCCTTG | R: CAGGGACCTTG |
|  | intron 11 | F: ACCAACGTGGA | F: ACCAATGTGGA |
|  |  | R: TCCACGTTGGT | R: TCCACATTGGT |
|  | exon 12 | F: TGGCATGAGGT | F: TGGCACGAGGT |
|  |  | R: ACCTCATGCCA | R: ACCTCGTGCCA |
|  | exon 13 | F: GGCACCGTAAG | F: GGCACTGTAAG |
|  |  | R: CTTACGGTGCC | R: CTTACAGTGCC |
|  | 3'UTR | F: ACTTCTGCTTT | F: ACTTCGGCTTT |
|  |  | R: AAAGCAGAAGT | R: AAAGCCGAAGT |
| CYP3A7 | exon 11 | F: TACTGGACAGAGC | F: TACTGGAGAGAGC |
|  |  | R: GCTCTGTCCAGTA | R: GCTCTCTCCAGTA |

TABLE 5

Testosterone hydroxylase activity of wild-type and mutant CYP3A4 proteins

|  | 25 μM Testosterone (nmol product/min/nmol protein) | | | 400 μM Testosterone (nmol product/min/nmol protein) | | |
|---|---|---|---|---|---|---|
| protein | 6β-OH | 15β-OH | 2β-OH | 6β-OH | 15β-OH | 2β-OH |
| WT | 9.3[a] | 0.4 | 0.2 | 41.6[a] | 1.2 | 3.0 |
| M1 | 5.1, 4.8[b] | 0.2, 0.2 | <0.1, <0.1 | 32.1, 32.2[b] | 1.2, 1.1 | 5.4, 6.9 |
| M4 | 4.4, 3.9 | 0.1, 0.1 | <0.1, <0.1 | 32.4, 29.8 | 1.3, 0.9 | 5.3, 5.6 |
| M5 | 5.1[c] | 0.1 | <0.1, <0.1 | 19.5[c] | 0.7 | 3.6 |
| M6 | 10.1, 8.6 | 1.7, 1.3 | 3.5, 2.8 | 45.3, 58.8 | 5.9, 7.7 | 29.2, 36.3 |

[a]Single values are the average of duplicates from assays performed with one preparation only.
[b]The two values represent separate protein preparations. Each value is the average of assays performed in duplicate.
[c]Only one preparation of MS was purified.

TABLE 6

Progesterone hydroxylase activity of wild-type and mutant CYP3A4 proteins

|  | 25 μM Progesterone (nmol product/min/nmol protein) | | | 150 μM Progesterone (nmol product/min/nmol protein) | | |
|---|---|---|---|---|---|---|
| Protein | 6β-OH | 16α-OH | 6β/16α | 6β-OH | 16α-OH | 6β/16α |
| WT | 12.1[a] | 1.7 | 7.1 | 32.1[a] | 6.4 | 5.0 |
| M1 | 7.8, 7.9[b] | 1.4, 1.4 | 5.6, 5.6 | 21.3, 21.3[b] | 4.2, 4.2 | 5.1, 5.1 |
| M4 | 5.5, 5.4 | 0.5, 0.5 | 11.0, 10.8 | 21.4, 18.4 | 3.9, 3.1 | 5.5, 5.9 |
| M5 | 5.9[c] | 0.6 | 9.8 | 16.6[c] | 3.1 | 5.4 |
| M6 | 15.8, 12.3 | 2.1, 1.6 | 7.5, 7.7 | 40.1, 49.8 | 5.1, 6.5 | 7.9, 7.7 |

TABLE 7

7-Benzyloxy-4-(trifluoromethyl)coumarin (7-BFC) debenzylase activity of wild-type and mutant CYP3A4 proteins

| Protein | 7-hydroxy-4-(trifluoromethyl)coumarin (nmol product/min/nmol protein) |
|---|---|
| WT | 6.5[a] |
| M1 | 8.8, 91[b] |

TABLE 7-continued

7-Benzyloxy-4-(trifluoromethyl)coumarin (7-BFC) debenzylase
activity of wild-type and mutant CYP3A4 proteins

| Protein | 7-hydroxy-4-(trifluoromethyl)coumarin (nmol product/min/nmol protein) |
|---------|-----------------------------------------------------------------------|
| M4      | 2.3, 1.9[b]                                                           |
| M5      | 2.9[c]                                                                |
| M6      | 4.5, 5.2[b]                                                           |

[a]Single values are the average of duplicates from assays performed with one preparation only.
[b]The two values represent separate protein preparations. Each value is the average of assays performed in duplicate.
[c]Only one preparation of M5 was purified.

REFERENCES (1) Daly, Toxicol Lett 102-103 (1998), 143-7
(2) Touw, Drug Metabol Drug Interact 14 (1997), 55-82
(3) Thummel, Annu Rev Pharmacol Toxicol 38 (1998), 389-430
(4) Cholerton, Trends Pharmacol Sci 13 (1992), 434-9
(5) Ketter, J Clin Psychopharmacol 15 (1995), 387-98
(6) Forrester, Proc Natl Acad Sci USA 87 (1990), 8306-10
(7) Paolini, Nature 398 (1999), 760-1
(8) Westlind, Biochem Biophys Res Commun 259 (1999), 201-5
(9) Jounaidi, Biochem Biophys Res Commun 221 (1996), 466-70
(10) Schuetz, Pharmacogenetics 4 (1994), 11-20
(11) Hunt, Clin Pharmacol Ther 51 (1992), 18-23
(12) Kashuba, Clin Pharmacol Ther 64 (1998), 269-77
(13) Peyronneau, Eur J Biochem 218 (1993), 355-61
(14) Rebbeck, J Natl Cancer Inst 90 (1998), 1225-9
(15) Felix, Proc Natl Acad Sci USA 95 (1998), 13176-81
(16) He, Biochemistry 36 (1997), 8831-9
(17) Szklarz, J Comput Aided Mol Des 11 (1997), 265-72
(18) Harlow, J Biol Chem 272 (1997), 5396-402
(19) Wang, Biochemistry 37 (1998), 12536-45
(20) Harlow, Proc Natl Acad Sci USA 95 (1998), 6636-41
(21) Domanski, Arch Biochem Biophys 350 (1998), 223-32
(22) Lehmann, J Clin Invest 102 (1998), 1016-23
(23) Bertilsson, Proc Natl Acad Sci USA 95 (1998), 12208-13
(24) Kliewer, Cell 92 (1998), 73-82
(25) Pascussi, Biochem Biophys Res Commun 260 (1999), 377-81

The invention claimed is:

1. An isolated polynucleotide selected from the group consisting of:
   (a) a polynucleotide comprising 15 nucleotides of SEQ ID NO: 154, wherein the 15 nucleotides comprises the nucleotide sequence of SEQ ID NO: 90; and
   (b) a polynucleotide encoding a polypeptide comprising the amino acid sequence of SEQ ID NO: 155.

2. A vector comprising the polynucleotide of claim 1.

3. The vector of claim 2, wherein the polynucleotide is operatively linked to expression control sequences allowing expression in prokaryotic or eukaryotic cells.

4. An isolated host cell genetically engineered with the polynucleotide of claim 1 or the vector of claim 2 or 3.

5. An isolated polynucleotide fully complementary to a polynucleotide of claim 1.

6. A vector comprising the nucleic acid molecule of claim 5.

7. A primer or probe selected from the group consisting of:
   (a) an oligonucleotide of about 15 to 50 nucleotides in length of SEQ ID NO: 154 comprising SEQ ID NO:90; and
   (b) an oligonucleotide that is fully complementary to the oligonucleotide of (a).

8. A composition comprising the polynucleotide of claim 1.

9. The composition of claim 8 which is a diagnostic composition.

10. An isolated polynucleotide selected from the group consisting of:
   (a) a polynucleotide comprising the nucleotide sequence of positions 162 to 176 of SEQ ID NO: 154;
   (b) a polynucleotide comprising the nucleotide sequence of positions 163 to 177 of SEQ ID NO: 154;
   (c) a polynucleotide comprising the nucleotide sequence of positions 164 to 178 of SEQ ID NO: 154;
   (d) a polynucleotide comprising the nucleotide sequence of positions 165 to 179 of SEQ ID NO: 154;
   (e) a polynucleotide comprising the nucleotide sequence of positions 166 to 180 of SEQ ID NO: 154;
   (f) a polynucleotide comprising the nucleotide sequence of the full complement of any of (a) to (e).

* * * * *

```
                        SEQUENCE LISTING

<160> NUMBER OF SEQ ID NOS: 172

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:  Synthetic
      Sequence

<400> SEQUENCE: 1
taatacgact cactataggg                                                    20

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence:  Synthetic
      Sequence

<400> SEQUENCE: 2
gaacccattc acatggac                                                      18

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence:  Synthetic
      Sequence

<400> SEQUENCE: 3
tgatcatgtc aggatctg                                                      18

<210> SEQ ID NO 4
<211> LENGTH: 18
<212> TYPE: DNA
<213> ORGANISM: Artificial Sequence
```

-continued

```
<220> FEATURE:
<223> OTHER INFORMATION: Description of Artificial Sequence: Synthetic
      Sequence

<400> SEQUENCE: 4
ggtcaacagc ctgtgctg                                                   18

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 5
tccactggtg aaggttgg                                                   18

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 6
gtgccatctc tatagctg                                                   18

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 7
cttcccgcct cagatttc                                                   18

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 8
gaaatctgag gcgggaag                                                   18

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 9
gggtcttgtg gattgttg                                                   18

<210> SEQ ID NO 10
<211> LENGTH: 18
<212> TYPE: DNA
<213> ORGANISM: Artificial Sequence
<220> FEATURE:
```

-continued

<223> OTHER INFORMATION: Description of Artificial Sequence: Synthetic
      Sequence

<400> SEQUENCE: 10
caacaatcca caagaccc                                                   18

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 11
gtgtatcttc gaggcgac                                                   18

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 12
ctttccattc ctcatccc                                                   18

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 13
cctttgtggg actcagtttc                                                 20

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 14
gccactcacc ctgatgtc                                                   18

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 15
atcaccaccc accctttg                                                   18

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Synthetic Sequence

<400> SEQUENCE: 16
caaagggtgg gtggtgat                                                        18

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 17
gagagcaaac ctcatgcc                                                        18

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 18
ggcatgaggt ttgctctc                                                        18

<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 19
ggtgccatcc cttgactc                                                        18

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 20
gcagaggtgt gggccctg                                                        18

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 21
ggagatcaag gaccacgctt gtg                                                  23

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 22
cttacgcttc tgccagtagc aacc                                              24

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 23
aacaggcgtg gaaacacaat                                                   20

<210> SEQ ID NO 24
<211> LENGTH: 18
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 24
ctttcctgcc ctgcacag                                                     18

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 25
aactgcaggc agagcacagg t                                                 21

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 26
ccacgcccgg cctgaacatc t                                                 21

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 27
taggatccaa tcatctccta c                                                 21

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: Synthetic
      Sequence

```
<400> SEQUENCE: 28
ggtgtctcat ggtggagg                                              18

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 29
agagttagca agagagccct t                                          21

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 30
cctctaactg ccagcaagtc tg                                         22

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 31
gcgctgagac tgtcctctgt g                                          21

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 32
agtctggctt cctgggttgg gctc                                       24

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 33
ggggacagga tgaagtggac g                                          21

<210> SEQ ID NO 34
<211> LENGTH: 19
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 34
```

-continued tacaaccatg gagacctcc                                             19

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 35
tacctgtccc caccagattc                                            20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 36
ccctttccaa ggggtagtcc                                            20

<210> SEQ ID NO 37
<211> LENGTH: 30
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 37
gtctggtcac tggaataacc caacagcagg                                 30

<210> SEQ ID NO 38
<211> LENGTH: 23
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 38
gtctgtcttg actggacatg tgg                                        23

<210> SEQ ID NO 39
<211> LENGTH: 22
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 39
gatgatggtc acacatatct tc                                         22

<210> SEQ ID NO 40
<211> LENGTH: 26
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 40
ggcttccagt tgagaacctt gatgtc							26

<210> SEQ ID NO 41
<211> LENGTH: 22
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 41
gctctaaaca tgagcagtct tc							22

<210> SEQ ID NO 42
<211> LENGTH: 23
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 42
ggagatcaag gaccacgctt gtg							23

<210> SEQ ID NO 43
<211> LENGTH: 25
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 43
ctcatcatcc tggaatactt cctgc							25

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 44
cccagtgtac ctctgaattg c								21

<210> SEQ ID NO 45
<211> LENGTH: 18
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 45
cagagccttc ctacatag								18

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 46
cagtatgagt tagtctctgg								20

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 47
cataactgat gaccttcatc g                                            21

<210> SEQ ID NO 48
<211> LENGTH: 22
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 48
cctgtgtact gctagtagag gg                                           22

<210> SEQ ID NO 49
<211> LENGTH: 18
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 49
cacagatggg cctaattg                                                18

<210> SEQ ID NO 50
<211> LENGTH: 24
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 50
ggagtgtctc actcactttg atgc                                         24

<210> SEQ ID NO 51
<211> LENGTH: 18
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 51
tggatgaagc ccatcttc                                                18

<210> SEQ ID NO 52
<211> LENGTH: 15
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 52
tcccagggct tttgt                                                   15

<210> SEQ ID NO 53
<211> LENGTH: 15
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 53
acaaaagccc tggga                                                     15

<210> SEQ ID NO 54
<211> LENGTH: 15
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 54
tcccaggact tttgt                                                     15

<210> SEQ ID NO 55
<211> LENGTH: 15
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 55
acaaaagtcc tggga                                                     15

<210> SEQ ID NO 56
<211> LENGTH: 14
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 56
tatctttctc tctt                                                      14

<210> SEQ ID NO 57
<211> LENGTH: 14
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 57
aagagagaaa gata                                                      14

<210> SEQ ID NO 58
<211> LENGTH: 14
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 58
tatcttgctc tctt                                                      14

```
<210> SEQ ID NO 59
<211> LENGTH: 14
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 59
aagagagcaa gata                                                       14

<210> SEQ ID NO 60
<211> LENGTH: 11
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 60
attacgatca t                                                          11

<210> SEQ ID NO 61
<211> LENGTH: 11
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 61
atgatcgtaa t                                                          11

<210> SEQ ID NO 62
<211> LENGTH: 11
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 62
attacaatca t                                                          11

<210> SEQ ID NO 63
<211> LENGTH: 11
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 63
atgattgtaa t                                                          11

<210> SEQ ID NO 64
<211> LENGTH: 11
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 64
agcctgtcac c                                                          11

<210> SEQ ID NO 65
```

```
<211> LENGTH: 11
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 65
ggtgacaggc t                                                          11

<210> SEQ ID NO 66
<211> LENGTH: 11
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 66
agcctatcac c                                                          11

<210> SEQ ID NO 67
<211> LENGTH: 11
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 67
ggtgataggc t                                                          11

<210> SEQ ID NO 68
<211> LENGTH: 11
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 68
tgaaagagta a                                                          11

<210> SEQ ID NO 69
<211> LENGTH: 11
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 69
ttactctttc a                                                          11

<210> SEQ ID NO 70
<211> LENGTH: 11
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 70
tgaaacagta a                                                          11

<210> SEQ ID NO 71
<211> LENGTH: 11
```

```
<212> TYPE: DNA
<213> ORGANISM: Artificial Sequence
<220> FEATURE:
<223> OTHER INFORMATION: Description of Artificial Sequence:  Synthetic
      Sequence

<400> SEQUENCE: 71
ttactgtttc a                                                              11

<210> SEQ ID NO 72
<211> LENGTH: 11
<212> TYPE: DNA
<213> ORGANISM: Artificial Sequence
<220> FEATURE:
<223> OTHER INFORMATION: Description of Artificial Sequence:  Synthetic
      Sequence

<400> SEQUENCE: 72
gcagccatgg g                                                              11

<210> SEQ ID NO 73
<211> LENGTH: 11
<212> TYPE: DNA
<213> ORGANISM: Artificial Sequence
<220> FEATURE:
<223> OTHER INFORMATION: Description of Artificial Sequence:  Synthetic
      Sequence

<400> SEQUENCE: 73
cccatggctg c                                                              11

<210> SEQ ID NO 74
<211> LENGTH: 11
<212> TYPE: DNA
<213> ORGANISM: Artificial Sequence
<220> FEATURE:
<223> OTHER INFORMATION: Description of Artificial Sequence:  Synthetic
      Sequence

<400> SEQUENCE: 74
gcagctatgg g                                                              11

<210> SEQ ID NO 75
<211> LENGTH: 11
<212> TYPE: DNA
<213> ORGANISM: Artificial Sequence
<220> FEATURE:
<223> OTHER INFORMATION: Description of Artificial Sequence:  Synthetic
      Sequence

<400> SEQUENCE: 75
cccatagctg c                                                              11

<210> SEQ ID NO 76
<211> LENGTH: 11
<212> TYPE: DNA
<213> ORGANISM: Artificial Sequence
<220> FEATURE:
<223> OTHER INFORMATION: Description of Artificial Sequence:  Synthetic
      Sequence

<400> SEQUENCE: 76
atggggttct g                                                              11

<210> SEQ ID NO 77
<211> LENGTH: 11
<212> TYPE: DNA
```

```
<213> ORGANISM: Artificial Sequence
<220> FEATURE:
<223> OTHER INFORMATION: Description of Artificial Sequence: Synthetic
      Sequence

<400> SEQUENCE: 77
cagaacccca t                                                              11

<210> SEQ ID NO 78
<211> LENGTH: 11
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 78
atgggtttct g                                                              11

<210> SEQ ID NO 79
<211> LENGTH: 11
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 79
cagaaaccca t                                                              11

<210> SEQ ID NO 80
<211> LENGTH: 11
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 80
ccagctgcct g                                                              11

<210> SEQ ID NO 81
<211> LENGTH: 11
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 81
caggcagctg g                                                              11

<210> SEQ ID NO 82
<211> LENGTH: 11
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 82
ccagcggcct g                                                              11

<210> SEQ ID NO 83
<211> LENGTH: 11
<212> TYPE: DNA
<213> ORGANISM: Artificial Sequence
```

-continued

```
<220> FEATURE:
<223> OTHER INFORMATION: Description of Artificial Sequence: Synthetic
      Sequence

<400> SEQUENCE: 83
caggccgctg g                                                              11

<210> SEQ ID NO 84
<211> LENGTH: 11
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 84
ggatggtaca t                                                              11

<210> SEQ ID NO 85
<211> LENGTH: 11
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 85
atgtaccatc c                                                              11

<210> SEQ ID NO 86
<211> LENGTH: 11
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 86
ggatgataca t                                                              11

<210> SEQ ID NO 87
<211> LENGTH: 11
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 87
atgtatcatc c                                                              11

<210> SEQ ID NO 88
<211> LENGTH: 11
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 88
tgaaacgctc a                                                              11

<210> SEQ ID NO 89
<211> LENGTH: 11
<212> TYPE: DNA
<213> ORGANISM: Artificial Sequence
<220> FEATURE:
```

-continued

<223> OTHER INFORMATION: Description of Artificial Sequence: Synthetic
      Sequence

<400> SEQUENCE: 89
tgagcgtttc a                                                                11

<210> SEQ ID NO 90
<211> LENGTH: 11
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 90
tgaaatgctc a                                                                11

<210> SEQ ID NO 91
<211> LENGTH: 11
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 91
tgagcatttc a                                                                11

<210> SEQ ID NO 92
<211> LENGTH: 11
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 92
gaaacgctca g                                                                11

<210> SEQ ID NO 93
<211> LENGTH: 11
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 93
ctgagcgttt c                                                                11

<210> SEQ ID NO 94
<211> LENGTH: 11
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 94
gaaacactca g                                                                11

<210> SEQ ID NO 95
<211> LENGTH: 11
<212> TYPE: DNA
<213> ORGANISM: Artificial Sequence
<220> FEATURE:
<223> OTHER INFORMATION: Description of Artificial Sequence: Synthetic -continued

```
        Sequence

<400> SEQUENCE: 95
ctgagtgttt c                                                              11

<210> SEQ ID NO 96
<211> LENGTH: 11
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 96
tgagacttga g                                                              11

<210> SEQ ID NO 97
<211> LENGTH: 11
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 97
ctcaagtctc a                                                              11

<210> SEQ ID NO 98
<211> LENGTH: 11
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 98
tgagatttga g                                                              11

<210> SEQ ID NO 99
<211> LENGTH: 11
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 99
ctcaaatctc a                                                              11

<210> SEQ ID NO 100
<211> LENGTH: 11
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 100
cctccctgaa a                                                              11

<210> SEQ ID NO 101
<211> LENGTH: 11
<212> TYPE: DNA
<213> ORGANISM: Artificial Sequence
<220> FEATURE:
<223> OTHER INFORMATION: Description of Artificial Sequence: Synthetic
      Sequence
```

```
<400> SEQUENCE: 101
tttcagggag g                                                          11

<210> SEQ ID NO 102
<211> LENGTH: 11
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 102
cctccttgaa a                                                          11

<210> SEQ ID NO 103
<211> LENGTH: 11
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 103
tttcaaggag g                                                          11

<210> SEQ ID NO 104
<211> LENGTH: 11
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 104
caaggcccct g                                                          11

<210> SEQ ID NO 105
<211> LENGTH: 11
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 105 cagggqccctt g                                                         11

<210> SEQ ID NO 106
<211> LENGTH: 11
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 106
caaggtccct g                                                          11

<210> SEQ ID NO 107
<211> LENGTH: 11
<212> TYPE: DNA
<213> ORGANISM: Artificial Sequence
<220> FEATURE:
<223> OTHER INFORMATION: Description of Artificial Sequence: Synthetic
      Sequence
```

```
<400> SEQUENCE: 107
cagggacctt g                                                          11

<210> SEQ ID NO 108
<211> LENGTH: 11
<212> TYPE: DNA
<213> ORGANISM: Artificial Sequence
<220> FEATURE:
<223> OTHER INFORMATION: Description of Artificial Sequence:  Synthetic
      Sequence

<400> SEQUENCE: 108
accaacgtgg a                                                          11

<210> SEQ ID NO 109
<211> LENGTH: 11
<212> TYPE: DNA
<213> ORGANISM: Artificial Sequence
<220> FEATURE:
<223> OTHER INFORMATION: Description of Artificial Sequence:  Synthetic
      Sequence

<400> SEQUENCE: 109
tccacgttgg t                                                          11

<210> SEQ ID NO 110
<211> LENGTH: 11
<212> TYPE: DNA
<213> ORGANISM: Artificial Sequence
<220> FEATURE:
<223> OTHER INFORMATION: Description of Artificial Sequence:  Synthetic
      Sequence

<400> SEQUENCE: 110
accaatgtgg a                                                          11

<210> SEQ ID NO 111
<211> LENGTH: 11
<212> TYPE: DNA
<213> ORGANISM: Artificial Sequence
<220> FEATURE:
<223> OTHER INFORMATION: Description of Artificial Sequence:  Synthetic
      Sequence

<400> SEQUENCE: 111
tccacattgg t                                                          11

<210> SEQ ID NO 112
<211> LENGTH: 11
<212> TYPE: DNA
<213> ORGANISM: Artificial Sequence
<220> FEATURE:
<223> OTHER INFORMATION: Description of Artificial Sequence:  Synthetic
      Sequence

<400> SEQUENCE: 112
tggcatgagg t                                                          11

<210> SEQ ID NO 113
<211> LENGTH: 11
<212> TYPE: DNA
<213> ORGANISM: Artificial Sequence
<220> FEATURE:
<223> OTHER INFORMATION: Description of Artificial Sequence:  Synthetic
      Sequence

<400> SEQUENCE: 113
```
acctcatgcc a    11

<210> SEQ ID NO 114
<211> LENGTH: 11
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 114
tggcacgagg t    11

<210> SEQ ID NO 115
<211> LENGTH: 11
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 115
acctcgtgcc a    11

<210> SEQ ID NO 116
<211> LENGTH: 11
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 116
ggcaccgtaa g    11

<210> SEQ ID NO 117
<211> LENGTH: 11
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 117
cttacggtgc c    11

<210> SEQ ID NO 118
<211> LENGTH: 11
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 118
ggcactgtaa g    11

<210> SEQ ID NO 119
<211> LENGTH: 11
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 119
cttacagtgc c                                                           11

<210> SEQ ID NO 120
<211> LENGTH: 11
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 120
acttctgctt t                                                           11

<210> SEQ ID NO 121
<211> LENGTH: 11
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 121
aaagcagaag t                                                           11

<210> SEQ ID NO 122
<211> LENGTH: 11
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 122
acttcggctt t                                                           11

<210> SEQ ID NO 123
<211> LENGTH: 11
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 123
aaagccgaag t                                                           11

<210> SEQ ID NO 124
<211> LENGTH: 13
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 124
tactggacag agc                                                         13

<210> SEQ ID NO 125
<211> LENGTH: 13
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 125
gctctgtcca gta                                                         13

<210> SEQ ID NO 126
<211> LENGTH: 13
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 126
tactggagag agc                                                        13

<210> SEQ ID NO 127
<211> LENGTH: 13
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 127
gctctctcca gta                                                        13

<210> SEQ ID NO 128
<211> LENGTH: 249
<212> TYPE: DNA
<213> ORGANISM: Homo sapiens
<220> FEATURE:
<221> NAME/KEY: intron
<222> LOCATION: (1)..(115)
<223> OTHER INFORMATION:
<220> FEATURE:
<221> NAME/KEY: exon
<222> LOCATION: (116)..(168)
<223> OTHER INFORMATION:
<220> FEATURE:
<221> NAME/KEY: intron
<222> LOCATION: (169)..(249)
<223> OTHER INFORMATION:
<220> FEATURE:
<221> NAME/KEY: CDS
<222> LOCATION: (116)..(166)
<223> OTHER INFORMATION:

<400> SEQUENCE: 128
cctctaactg ccagcaagtc tgatttcatt ggcttcgact gttttcatcc aattagagg       60 cagggttaag tacattaaaa ataataatca aatattattt tgtttctcct cccag grc     118
                                                               Xaa
                                                                 1 ttt tgt atg ttt gac atg gaa tgt cat aaa aag tat gga aaa gtg tgg      166
Phe Cys Met Phe Asp Met Glu Cys His Lys Lys Tyr Gly Lys Val Trp
            5                  10                  15 gggtgagtat tctggaaact tccattggat agacttgttt ctatgatgag tttaccccac    226
tgcacagagg acagtctcag ccc                                            249

<210> SEQ ID NO 129
<211> LENGTH: 17
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is Gly or Asp

<400> SEQUENCE: 129

Xaa Phe Cys Met Phe Asp Met Glu Cys His Lys Lys Tyr Gly Lys Val
 1               5                  10                  15

Trp

<210> SEQ ID NO 130
<211> LENGTH: 293
<212> TYPE: DNA
<213> ORGANISM: Homo sapiens
<220> FEATURE:
<221> NAME/KEY: intron
<222> LOCATION: (1)..(77)
<223> OTHER INFORMATION:
<220> FEATURE:
<221> NAME/KEY: exon
<222> LOCATION: (78)..(177)
<223> OTHER INFORMATION:
<220> FEATURE:
<221> NAME/KEY: intron
<222> LOCATION: (178)..(293)
<223> OTHER INFORMATION:
<220> FEATURE:
<221> NAME/KEY: CDS
<222> LOCATION: (79)..(177)
<223> OTHER INFORMATION:

<400> SEQUENCE: 130

```
agtctggctt cctgggttgg gctccagctg tagaataagg ctgttgatgt ttaatcaact    60 ctgtttttt cacacagc ttt tat gat ggt caa cag cct gtg ctg gct atc     111
                  Phe Tyr Asp Gly Gln Gln Pro Val Leu Ala Ile
                   1               5                  10 aca gat cct gac atg atc aaa aca gtg cta gtg aaa gaa tgt tat tct    159
Thr Asp Pro Asp Met Ile Lys Thr Val Leu Val Lys Glu Cys Tyr Ser
         15                  20                  25 gtc ttc aca aac cgg agg gtaagcattc atgtgttgaa attaaaatac            207
Val Phe Thr Asn Arg Arg
            30 tgattgatta aatttatatt ttgaaattct tatatattca tagacagttg cctaaaaaat   267 gtccaggaag gttccacgtc cacttc                                       293
```

<210> SEQ ID NO 131
<211> LENGTH: 33
<212> TYPE: PRT
<213> ORGANISM: Homo sapiens

<400> SEQUENCE: 131

```
Phe Tyr Asp Gly Gln Gln Pro Val Leu Ala Ile Thr Asp Pro Asp Met
 1               5                  10                  15

Ile Lys Thr Val Leu Val Lys Glu Cys Tyr Ser Val Phe Thr Asn Arg
            20                  25                  30
```

Arg

<210> SEQ ID NO 132
<211> LENGTH: 236
<212> TYPE: DNA
<213> ORGANISM: Homo sapiens
<220> FEATURE:
<221> NAME/KEY: intron
<222> LOCATION: (1)..(61)
<223> OTHER INFORMATION:
<220> FEATURE:
<221> NAME/KEY: exon
<222> LOCATION: (62)..(175)
<223> OTHER INFORMATION:
<220> FEATURE:
<221> NAME/KEY: intron
<222> LOCATION: (176)..(236)
<223> OTHER INFORMATION:
<220> FEATURE:

```
<221> NAME/KEY: CDS
<222> LOCATION: (62)..(175)
<223> OTHER INFORMATION:

<400> SEQUENCE: 132
ctacaaccat ggagacctcc acaactgatg taggacaaaa tgtttctgct ttgaactcta    60 g cct ttt ggt cca gtg gga ttt atg aaa agt gcc atc tct ata gct gag  109
  Pro Phe Gly Pro Val Gly Phe Met Lys Ser Ala Ile Ser Ile Ala Glu
    1               5                  10                  15 gat gaa gaa tgg aag aga tta cga tca ttg ctg tct cca acc ttc acc    157
Asp Glu Glu Trp Lys Arg Leu Arg Ser Leu Leu Ser Pro Thr Phe Thr
             20                  25                  30 agt gga aaa ctc aag gag gtatgaaaat aacatgagtt ttaataagaa           205
Ser Gly Lys Leu Lys Glu
         35 acttaaagaa tgaatctggt ggggacaggt a                                 236

<210> SEQ ID NO 133
<211> LENGTH: 38
<212> TYPE: PRT
<213> ORGANISM: Homo sapiens

<400> SEQUENCE: 133

Pro Phe Gly Pro Val Gly Phe Met Lys Ser Ala Ile Ser Ile Ala Glu
  1               5                  10                  15

Asp Glu Glu Trp Lys Arg Leu Arg Ser Leu Leu Ser Pro Thr Phe Thr
             20                  25                  30

Ser Gly Lys Leu Lys Glu
         35

<210> SEQ ID NO 134
<211> LENGTH: 393
<212> TYPE: DNA
<213> ORGANISM: Homo sapiens
<220> FEATURE:
<221> NAME/KEY: intron
<222> LOCATION: (1)..(98)
<223> OTHER INFORMATION:
<220> FEATURE:
<221> NAME/KEY: exon
<222> LOCATION: (99)..(247)
<223> OTHER INFORMATION:
<220> FEATURE:
<221> NAME/KEY: intron
<222> LOCATION: (248)..(393)
<223> OTHER INFORMATION:
<220> FEATURE:
<221> NAME/KEY: CDS
<222> LOCATION: (100)..(246)
<223> OTHER INFORMATION:

<400> SEQUENCE: 134
gtctgtcttg actggacatg tggctttcct gatgcacgca tagaggaagg atggtaaaaa   60
ggtgctgatt ttaattttcc acatctttct ccactcagc gtc ttt ggg gcc tac    114
                                            Val Phe Gly Ala Tyr
                                              1               5 agc atg gat gtg atc act agc aca tca ttt gga gtg aac atc gac tct   162
Ser Met Asp Val Ile Thr Ser Thr Ser Phe Gly Val Asn Ile Asp Ser
             10                  15                  20 ctc aac aat cca caa gac ccc ttt gtg gaa aac acc aag aag ctt tta   210
Leu Asn Asn Pro Gln Asp Pro Phe Val Glu Asn Thr Lys Lys Leu Leu
         25                  30                  35 aga ttt gat ttt ttg gat cca ttc ttt ctc tca ata agtatgtgga        256
Arg Phe Asp Phe Leu Asp Pro Phe Phe Leu Ser Ile
```

```
ctactatttc cttttattta tcttkctctc ttaaaaataa ctgctttatt gagatataaa    316
tcaccatgta attcatccac ttaaaatata cagttcagtg atttgtagta catttgaaga    376
tatgtgtgac catcatc                                                   393
```

<210> SEQ ID NO 135
<211> LENGTH: 49
<212> TYPE: PRT
<213> ORGANISM: Homo sapiens

<400> SEQUENCE: 135

```
Val Phe Gly Ala Tyr Ser Met Asp Val Ile Thr Ser Thr Ser Phe Gly
 1               5                  10                  15

Val Asn Ile Asp Ser Leu Asn Asn Pro Gln Asp Pro Phe Val Glu Asn
            20                  25                  30

Thr Lys Lys Leu Leu Arg Phe Asp Phe Leu Asp Pro Phe Phe Leu Ser
        35                  40                  45

Ile
```

<210> SEQ ID NO 136
<211> LENGTH: 240
<212> TYPE: DNA
<213> ORGANISM: Homo sapiens
<220> FEATURE:
<221> NAME/KEY: intron
<222> LOCATION: (1)..(82)
<223> OTHER INFORMATION:
<220> FEATURE:
<221> NAME/KEY: exon
<222> LOCATION: (83)..(149)
<223> OTHER INFORMATION:
<220> FEATURE:
<221> NAME/KEY: intron
<222> LOCATION: (150)..(240)
<223> OTHER INFORMATION:
<220> FEATURE:
<221> NAME/KEY: CDS
<222> LOCATION: (83)..(148)
<223> OTHER INFORMATION:

<400> SEQUENCE: 136

```
ggagatcaag gaccacgctt gtgatttact tctgacttca ggagccactt tctgtcagtg    60
aaatttctct ttttgcttct ag cac cga gtg gat ttc ctt cag ctg atg att   112
                         His Arg Val Asp Phe Leu Gln Leu Met Ile
                          1               5                  10 gac tct cag aat tca aaa gaa act gag tcc cac aaa ggtaaccaga          158
Asp Ser Gln Asn Ser Lys Glu Thr Glu Ser His Lys
             15                  20 gtgtttctga gggctacttg tggggcactc agagggaagg ccttgttctg aaaatgtgca    218
ggaagtattc caggatgatg ag                                             240
```

<210> SEQ ID NO 137
<211> LENGTH: 22
<212> TYPE: PRT
<213> ORGANISM: Homo sapiens

<400> SEQUENCE: 137

```
His Arg Val Asp Phe Leu Gln Leu Met Ile Asp Ser Gln Asn Ser Lys
 1               5                  10                  15

Glu Thr Glu Ser His Lys
            20
```

```
<210> SEQ ID NO 138
<211> LENGTH: 399
<212> TYPE: DNA
<213> ORGANISM: Homo sapiens
<220> FEATURE:
<221> NAME/KEY: intron
<222> LOCATION: (1)..(111)
<223> OTHER INFORMATION:
<220> FEATURE:
<221> NAME/KEY: exon
<222> LOCATION: (112)..(338)
<223> OTHER INFORMATION:
<220> FEATURE:
<221> NAME/KEY: intron
<222> LOCATION: (339)..(399)
<223> OTHER INFORMATION:
<220> FEATURE:
<221> NAME/KEY: CDS
<222> LOCATION: (112)..(336)
<223> OTHER INFORMATION:

<400> SEQUENCE: 138
ccagtatgag ttgttctctg gaacttctaa cagttcaaca gtactacatg gactgagtta      60
aaagttaatt caaaaatctc aatttatcca aatctgtttc tttcttttca g gca cca     117
                                                         Ala Pro
                                                          1 ccc acc tat gat act gtg cta cag atg gag tat ctt gac atg gtg gtg     165
Pro Thr Tyr Asp Thr Val Leu Gln Met Glu Tyr Leu Asp Met Val Val
     5                  10                  15 aat gaa acg ctc aga tta ttc cca att gct atg aga ctt gag agg gtc     213
Asn Glu Thr Leu Arg Leu Phe Pro Ile Ala Met Arg Leu Glu Arg Val
 20                  25                  30 tgc aaa aaa gat gtt gag atc aat ggg atg ttc att ccc aaa ggg tgg     261
Cys Lys Lys Asp Val Glu Ile Asn Gly Met Phe Ile Pro Lys Gly Trp
 35                  40                  45                  50 gtg gtg atg att cca agc tat gct ctt cac cgt gac cca aag tac tgg     309
Val Val Met Ile Pro Ser Tyr Ala Leu His Arg Asp Pro Lys Tyr Trp
             55                  60                  65 asa gag cct gag aag ttc ctc cct gaa aggtaggagg cccctgggaa            356
Xaa Glu Pro Glu Lys Phe Leu Pro Glu
             70                  75 gggagccctc cctgaaccag cctggttcaa gcatattctg cct                      399

<210> SEQ ID NO 139
<211> LENGTH: 75
<212> TYPE: PRT
<213> ORGANISM: Homo sapiens
<220> FEATURE:
<221> NAME/KEY: MISC_FEATURE
<222> LOCATION: (67)..(67)
<223> OTHER INFORMATION: Xaa is Thr or Arg

<400> SEQUENCE: 139

Ala Pro Pro Thr Tyr Asp Thr Val Leu Gln Met Glu Tyr Leu Asp Met
 1               5                  10                  15

Val Val Asn Glu Thr Leu Arg Leu Phe Pro Ile Ala Met Arg Leu Glu
             20                  25                  30

Arg Val Cys Lys Lys Asp Val Glu Ile Asn Gly Met Phe Ile Pro Lys
         35                  40                  45

Gly Trp Val Val Met Ile Pro Ser Tyr Ala Leu His Arg Asp Pro Lys
     50                  55                  60

Tyr Trp Xaa Glu Pro Glu Lys Phe Leu Pro Glu
 65                  70                  75
```

<210> SEQ ID NO 140
<211> LENGTH: 21
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 140
ccagtatgag ttgttctctg g                                            21

<210> SEQ ID NO 141
<211> LENGTH: 24
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 141
aggcagaata tgcttgaacc aggc                                         24

<210> SEQ ID NO 142
<211> LENGTH: 26
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 142
gaagtggacg tggaaccttc ctggac                                       26

<210> SEQ ID NO 143
<211> LENGTH: 304
<212> TYPE: DNA
<213> ORGANISM: Homo sapiens

<400> SEQUENCE: 143
agtctggctt cctgggttgg gctccagctg tagaataagg ctgttgatgt ttaatcaact    60
ctgttttttt cacacagctt ttatgatggt caacagcctg tgctggctat cacagatcct   120
gacatgatca aaacagtgct agtgaaagaa tgttattctg tcttcacaaa ccggagggta   180
agcattcatg tgttgaaatt aaaatactga ttgattaaat ttatattttg aaattcttat   240
atattcatag acagttgcct aaaaaatgtc caggaaggtt ccacgtccac ttcatcctgt   300
cccc                                                              304

<210> SEQ ID NO 144
<211> LENGTH: 236
<212> TYPE: DNA
<213> ORGANISM: Homo sapiens
<220> FEATURE:
<221> NAME/KEY: CDS
<222> LOCATION: (62)..(175)
<220> FEATURE:
<221> NAME/KEY: intron
<222> LOCATION: (1)..(61)
<220> FEATURE:
<221> NAME/KEY: intron
<222> LOCATION: (176)..(236)
<220> FEATURE:
<221> NAME/KEY: exon
<222> LOCATION: (62)..(175)

<400> SEQUENCE: 144

```
ctacaaccat ggagacctcc acaactgatg taggacaaaa tgtttctgct ttgaactcta      60 g cct ttt ggt cca gtg gga ttt atg aaa agt gcc atc tct ata gct gag    109
  Pro Phe Gly Pro Val Gly Phe Met Lys Ser Ala Ile Ser Ile Ala Glu
   1               5                  10                  15 gat gaa gaa tgg aag aga tta caa tca ttg ctg tct cca acc ttc acc      157
Asp Glu Glu Trp Lys Arg Leu Gln Ser Leu Leu Ser Pro Thr Phe Thr
             20                  25                  30 agt gga aaa ctc aag gag gtatgaaaat aacatgagtt ttaataagaa              205
Ser Gly Lys Leu Lys Glu
         35 acttaaagaa tgaatctggt ggggacaggt a                                    236

<210> SEQ ID NO 145
<211> LENGTH: 38
<212> TYPE: PRT
<213> ORGANISM: Homo sapiens

<400> SEQUENCE: 145

Pro Phe Gly Pro Val Gly Phe Met Lys Ser Ala Ile Ser Ile Ala Glu
 1               5                  10                  15

Asp Glu Glu Trp Lys Arg Leu Gln Ser Leu Leu Ser Pro Thr Phe Thr
            20                  25                  30

Ser Gly Lys Leu Lys Glu
         35

<210> SEQ ID NO 146
<211> LENGTH: 379
<212> TYPE: DNA
<213> ORGANISM: Homo sapiens
<220> FEATURE:
<221> NAME/KEY: CDS
<222> LOCATION: (188)..(274)

<400> SEQUENCE: 146
ccctttccaa ggggtagtcc actgaatttg agctgcctaa aaatggtctt ttatctttat     60
gtacagaaaa cacatcacaa aattcattat aaaatgtcac ttactgctcc atgctgggga    120
aagccatgtc cttctgggac tagagtctgc acatttaact atgggtggtg ttgtgttttg    180 tgcttag atg gtc cct atc att gcc cag tat gga gat gtg ttg gtg aga     229
        Met Val Pro Ile Ile Ala Gln Tyr Gly Asp Val Leu Val Arg
         1               5                  10 aat ctg agg cgg gaa gca gag aca ggc aag cct atc acc ttg aaa         274
Asn Leu Arg Arg Glu Ala Glu Thr Gly Lys Pro Ile Thr Leu Lys
 15                  20                  25 gagtaagtag aagcgcagcc atggggttct gagctgtcat gaacccctcc agctgcctgc    334
catggagctg atattcctgc tgttgggtta ttccagtgac cagac                    379

<210> SEQ ID NO 147
<211> LENGTH: 29
<212> TYPE: PRT
<213> ORGANISM: Homo sapiens

<400> SEQUENCE: 147

Met Val Pro Ile Ile Ala Gln Tyr Gly Asp Val Leu Val Arg Asn Leu
 1               5                  10                  15

Arg Arg Glu Ala Glu Thr Gly Lys Pro Ile Thr Leu Lys
            20                  25

<210> SEQ ID NO 148
<211> LENGTH: 379
```

```
<212> TYPE: DNA
<213> ORGANISM: Homo sapiens
<220> FEATURE:
<221> NAME/KEY: CDS
<222> LOCATION: (188)..(274)

<400> SEQUENCE: 148
ccctttccaa ggggtagtcc actgaatttg agctgcctaa aaatggtctt ttatctttat      60
gtacagaaaa cacatcacaa aattcattat aaaatgtcac ttactgctcc atgctggga     120 aagccatgtc cttctgggac tagagtctgc acatttaact atgggtggtg ttgtgttttg    180 tgcttag atg gtc cct atc att gcc cag tat gga gat gtg ttg gtg aga      229
        Met Val Pro Ile Ile Ala Gln Tyr Gly Asp Val Leu Val Arg
          1               5                  10 aat ctg agg cgg gaa gca gag aca ggc aag cct gtc acc ttg aaa          274
Asn Leu Arg Arg Glu Ala Glu Thr Gly Lys Pro Val Thr Leu Lys
 15                  20                  25 cagtaagtag aagcgcagcc atggggttct gagctgtcat gaacccctcc agctgcctgc    334
catggagctg atattcctgc tgttgggtta ttccagtgac cagac                    379

<210> SEQ ID NO 149
<211> LENGTH: 29
<212> TYPE: PRT
<213> ORGANISM: Homo sapiens

<400> SEQUENCE: 149

Met Val Pro Ile Ile Ala Gln Tyr Gly Asp Val Leu Val Arg Asn Leu
  1               5                  10                  15

Arg Arg Glu Ala Glu Thr Gly Lys Pro Val Thr Leu Lys
             20                  25

<210> SEQ ID NO 150
<211> LENGTH: 379
<212> TYPE: DNA
<213> ORGANISM: Homo sapiens

<400> SEQUENCE: 150
ccctttccaa ggggtagtcc actgaatttg agctgcctaa aaatggtctt ttatctttat      60
gtacagaaaa cacatcacaa aattcattat aaaatgtcac ttactgctcc atgctggga     120 aagccatgtc cttctgggac tagagtctgc acatttaact atgggtggtg ttgtgttttg    180
tgcttagatg gtccctatca ttgcccagta tggagatgtg ttggtgagaa atctgaggcg    240
ggaagcagag acaggcaagc ctgtcacctt gaaagagtaa gtagaagcgc agctatgggg    300
ttctgagctg tcatgaaccc ctccagctgc tgccatgga gctgatattc ctgctgttgg     360
gttattccag tgaccagac                                                  379

<210> SEQ ID NO 151
<211> LENGTH: 379
<212> TYPE: DNA
<213> ORGANISM: Homo sapiens

<400> SEQUENCE: 151
ccctttccaa ggggtagtcc actgaatttg agctgcctaa aaatggtctt ttatctttat      60
gtacagaaaa cacatcacaa aattcattat aaaatgtcac ttactgctcc atgctggga     120 aagccatgtc cttctgggac tagagtctgc acatttaact atgggtggtg ttgtgttttg    180
tgcttagatg gtccctatca ttgcccagta tggagatgtg ttggtgagaa atctgaggcg    240
ggaagcagag acaggcaagc ctgtcacctt gaaagagtaa gtagaagcgc agccatgggt    300
```

```
ttctgagctg tcatgaaccc ctccagctgc ctgccatgga gctgatattc ctgctgttgg      360
gttattccag tgaccagac                                                   379

<210> SEQ ID NO 152
<211> LENGTH: 379
<212> TYPE: DNA
<213> ORGANISM: Homo sapiens

<400> SEQUENCE: 152
ccctttccaa ggggtagtcc actgaatttg agctgcctaa aaatggtctt ttatctttat       60
gtacagaaaa cacatcacaa aattcattat aaaatgtcac ttactgctcc atgctgggga     120
aagccatgtc cttctgggac tagagtctgc acatttaact atgggtggtg ttgtgttttg     180
tgcttagatg gtccctatca ttgcccagta tggagatgtg ttggtgagaa atctgaggcg     240
ggaagcagag acaggcaagc ctgtcacctt gaaagagtaa gtagaagcgc agccatgggg     300
ttctgagctg tcatgaaccc ctccagcggc ctgccatgga gctgatattc ctgctgttgg     360
gttattccag tgaccagac                                                   379

<210> SEQ ID NO 153
<211> LENGTH: 431
<212> TYPE: DNA
<213> ORGANISM: Homo sapiens

<400> SEQUENCE: 153
cccagtgtac ctctgaattg cttttctatt cttttcccct agggatttga gggcttcact       60
tagatttctc ttcatctaaa ctgtgatgcc ctacattgat ctgatttacc taaaatgtct     120
ttcctctcct ttcagctctg tccgatctgg agctcgtggc ccaatcaatt atctttattt     180
ttgctggcta tgaaaccacg agcagtgttc tctccttcat tatgtatgaa ctggccactc     240
accctgatgt ccagcagaaa ctgcaggagg aaattgatgc agttttaccc aataaggtga     300
gtggatgata catggagaag gagggaggag gtgaaacctt agcaaaaatg cctcctcacc     360
acttcccagg agaattttta taaaaagcat aatcactgat tctttcactg actctatgta     420
ggaaggctct g                                                           431

<210> SEQ ID NO 154
<211> LENGTH: 574
<212> TYPE: DNA
<213> ORGANISM: Homo sapiens
<220> FEATURE:
<221> NAME/KEY: CDS
<222> LOCATION: (110)..(334)

<400> SEQUENCE: 154
cagtatgagt tagtctctgg agctcctaat acttcattag tactgcatgg actgagttaa       60
aagttaattc aaaatctcaa tttatccaaa tctgtttcgt tctttccag gca cca ccc     118
                                                        Ala Pro Pro
                                                          1 acc tat gat act gtg cta cag atg gag tat ctt gac atg gtg gtg aat       166
Thr Tyr Asp Thr Val Leu Gln Met Glu Tyr Leu Asp Met Val Val Asn
        5                   10                  15 gaa atg ctc aga tta ttc cca att gct atg aga ctt gag agg gtc tgc       214
Glu Met Leu Arg Leu Phe Pro Ile Ala Met Arg Leu Glu Arg Val Cys
 20                  25                  30                  35 aaa aaa gat gtt gag atc aat ggg atg ttc att ccc aaa ggg gtg gtg       262
Lys Lys Asp Val Glu Ile Asn Gly Met Phe Ile Pro Lys Gly Val Val
                40                  45                  50
```

```
gtg atg att cca agc tat gct ctt cac cgt gac cca aag tac tgg aca    310
Val Met Ile Pro Ser Tyr Ala Leu His Arg Asp Pro Lys Tyr Trp Thr
         55                  60                  65 gag cct gag aag ttc ctc cct gaa aggtacaagg ccctgggaa gggagccctc    364
Glu Pro Glu Lys Phe Leu Pro Glu
         70                  75 cctgaaccag cctggttcaa gcatattctg cctctcttaa tctacaggac agtcatgtgg    424
ttgtataatt atttgcttgt atttttatat ttagagattt ttttaatcat caaattgatt    484
attgtcacac tttacaaacc atagactaga aaaagaaaa ctacagtcat ccacaattcc    544
aacaacttac gatgaaggtc atcagttatg                                    574
```

<210> SEQ ID NO 155
<211> LENGTH: 75
<212> TYPE: PRT
<213> ORGANISM: Homo sapiens
<400> SEQUENCE: 155

```
Ala Pro Pro Thr Tyr Asp Thr Val Leu Gln Met Glu Tyr Leu Asp Met
 1               5                  10                  15

Val Val Asn Glu Met Leu Arg Leu Phe Pro Ile Ala Met Arg Leu Glu
             20                  25                  30

Arg Val Cys Lys Lys Asp Val Glu Ile Asn Gly Met Phe Ile Pro Lys
         35                  40                  45

Gly Val Val Met Ile Pro Ser Tyr Ala Leu His Arg Asp Pro Lys
     50                  55                  60

Tyr Trp Thr Glu Pro Glu Lys Phe Leu Pro Glu
 65                  70                  75
```

<210> SEQ ID NO 156
<211> LENGTH: 574
<212> TYPE: DNA
<213> ORGANISM: Homo sapiens
<400> SEQUENCE: 156

```
cagtatgagt tagtctctgg agctcctaat acttcattag tactgcatgg actgagttaa     60
aagttaattc aaaatctcaa tttatccaaa tctgtttcgt tctttccagg caccacccac    120
ctatgatact gtgctacaga tggagtatct tgacatggtg gtgaatgaaa cactcagatt    180
attcccaatt gctatgagac ttgagagggt ctgcaaaaaa gatgttgaga tcaatgggat    240
gttcattccc aaaggggtgg tggtgatgat tccaagctat gctcttcacc gtgacccaaa    300
gtactggaca gagcctgaga agttcctccc tgaaaggtac aaggcccctg ggaagggagc    360
cctccctgaa ccagcctggt tcaagcatat tctgcctctc ttaatctaca ggacagtcat    420
gtggttgtat aattatttgc ttgtattttt atatttagag attttttaa tcatcaaatt    480 gattattgtc acactttaca aaccatagac tagaaaaaag aaaactacag tcatccacaa    540
ttccaacaac ttacgatgaa ggtcatcagt tatg                                574
```

<210> SEQ ID NO 157
<211> LENGTH: 574
<212> TYPE: DNA
<213> ORGANISM: Homo sapiens
<220> FEATURE:
<221> NAME/KEY: CDS
<222> LOCATION: (110)..(334)

<400> SEQUENCE: 157

```
cagtatgagt tagtctctgg agctcctaat acttcattag tactgcatgg actgagttaa      60
aagttaattc aaaatctcaa tttatccaaa tctgtttcgt tctttccag gca cca ccc     118
                                                      Ala Pro Pro
                                                       1 acc tat gat act gtg cta cag atg gag tat ctt gac atg gtg gtg aat       166
Thr Tyr Asp Thr Val Leu Gln Met Glu Tyr Leu Asp Met Val Val Asn
     5                  10                  15 gaa acg ctc aga tta ttc cca att gct atg aga ttt gag agg gtc tgc       214
Glu Thr Leu Arg Leu Phe Pro Ile Ala Met Arg Phe Glu Arg Val Cys
 20                  25                  30                  35 aaa aaa gat gtt gag atc aat ggg atg ttc att ccc aaa ggg gtg gtg       262
Lys Lys Asp Val Glu Ile Asn Gly Met Phe Ile Pro Lys Gly Val Val
                 40                  45                  50 gtg atg att cca agc tat gct ctt cac cgt gac cca aag tac tgg aca       310
Val Met Ile Pro Ser Tyr Ala Leu His Arg Asp Pro Lys Tyr Trp Thr
             55                  60                  65 gag cct gag aag ttc ctc cct gaa aggtacaagg cccctgggaa gggagccctc      364
Glu Pro Glu Lys Phe Leu Pro Glu
             70              75 cctgaaccag cctggttcaa gcatattctg cctctcttaa tctacaggac agtcatgtgg     424
ttgtataatt atttgcttgt atttttatat ttagagattt ttttaatcat caaattgatt     484
attgtcacac ttacaaaacc atagactaga aaaagaaaaa ctacagtcat ccacaattcc     544
aacaacttac gatgaaggtc atcagttatg                                      574

<210> SEQ ID NO 158
<211> LENGTH: 75
<212> TYPE: PRT
<213> ORGANISM: Homo sapiens

<400> SEQUENCE: 158

Ala Pro Pro Thr Tyr Asp Thr Val Leu Gln Met Glu Tyr Leu Asp Met
 1               5                  10                  15

Val Val Asn Glu Thr Leu Arg Leu Phe Pro Ile Ala Met Arg Phe Glu
             20                  25                  30

Arg Val Cys Lys Lys Asp Val Glu Ile Asn Gly Met Phe Ile Pro Lys
         35                  40                  45

Gly Val Val Met Ile Pro Ser Tyr Ala Leu His Arg Asp Pro Lys
     50                  55                  60

Tyr Trp Thr Glu Pro Glu Lys Phe Leu Pro Glu
 65                  70                  75

<210> SEQ ID NO 159
<211> LENGTH: 574
<212> TYPE: DNA
<213> ORGANISM: Homo sapiens
<220> FEATURE:
<221> NAME/KEY: CDS
<222> LOCATION: (110)..(334)

<400> SEQUENCE: 159
cagtatgagt tagtctctgg agctcctaat acttcattag tactgcatgg actgagttaa      60
aagttaattc aaaatctcaa tttatccaaa tctgtttcgt tctttccag gca cca ccc     118
                                                      Ala Pro Pro
                                                       1 acc tat gat act gtg cta cag atg gag tat ctt gac atg gtg gtg aat       166
Thr Tyr Asp Thr Val Leu Gln Met Glu Tyr Leu Asp Met Val Val Asn
     5                  10                  15 gaa acg ctc aga tta ttc cca att gct atg aga ctt gag agg gtc tgc       214
```

```
Glu Thr Leu Arg Leu Phe Pro Ile Ala Met Arg Leu Glu Arg Val Cys
 20                  25                  30                  35 aaa aaa gat gtt gag atc aat ggg atg ttc att ccc aaa ggg gtg gtg      262
Lys Lys Asp Val Glu Ile Asn Gly Met Phe Ile Pro Lys Gly Val Val
             40                  45                  50 gtg atg att cca agc tat gct ctt cac cgt gac cca aag tac tgg aca      310
Val Met Ile Pro Ser Tyr Ala Leu His Arg Asp Pro Lys Tyr Trp Thr
         55                  60                  65 gag cct gag aag ttc ctc ctt gaa aggtacaagg cccctgggaa gggagccctc     364
Glu Pro Glu Lys Phe Leu Leu Glu
     70                  75 cctgaaccag cctggttcaa gcatattctg cctctcttaa tctacaggac agtcatgtgg    424
ttgtataatt atttgcttgt atttttatat ttagagattt ttttaatcat caaattgatt    484
attgtcacac tttacaaacc atagactaga aaaagaaaa ctacagtcat ccacaattcc     544
aacaacttac gatgaaggtc atcagttatg                                     574
```

<210> SEQ ID NO 160
<211> LENGTH: 75
<212> TYPE: PRT
<213> ORGANISM: Homo sapiens

<400> SEQUENCE: 160

```
Ala Pro Pro Thr Tyr Asp Thr Val Leu Gln Met Glu Tyr Leu Asp Met
 1               5                  10                  15

Val Val Asn Glu Thr Leu Arg Leu Phe Pro Ile Ala Met Arg Leu Glu
             20                  25                  30

Arg Val Cys Lys Lys Asp Val Glu Ile Asn Gly Met Phe Ile Pro Lys
         35                  40                  45

Gly Val Val Val Met Ile Pro Ser Tyr Ala Leu His Arg Asp Pro Lys
     50                  55                  60

Tyr Trp Thr Glu Pro Glu Lys Phe Leu Leu Glu
 65                  70                  75
```

<210> SEQ ID NO 161
<211> LENGTH: 574
<212> TYPE: DNA
<213> ORGANISM: Homo sapiens

<400> SEQUENCE: 161

```
cagtatgagt tagtctctgg agctcctaat acttcattag tactgcatgg actgagttaa      60
aagttaattc aaaatctcaa tttatccaaa tctgtttcgt tctttccagg caccacccac     120
ctatgatact gtgctacaga tggagtatct tgacatggtg gtgaatgaaa cgctcagatt     180
attcccaatt gctatgagac ttgagagggt ctgcaaaaaa gatgttgaga tcaatgggat     240
gttcattccc aaaggggtgg tggtgatgat tccaagctat gctcttcacc gtgacccaaa     300
gtactggaca gagcctgaga agttcctccc tgaaggtac aaggtccctg ggaagggagc      360
cctccctgaa ccagcctggt tcaagcatat tctgcctctc ttaatctaca ggacagtcat     420
gtggttgtat aattatttgc ttgtattttt atatttagag attttttta tcatcaaatt     480 gattattgtc acactttaca aaccatagac tagaaaaaag aaaactacag tcatccacaa     540
ttccaacaac ttacgatgaa ggtcatcagt tatg                                574
```

<210> SEQ ID NO 162
<211> LENGTH: 411
<212> TYPE: DNA
<213> ORGANISM: Homo sapiens

<400> SEQUENCE: 162

```
cctgtgtact actagttgag gggtggcccc taagtaagaa accctaacat gtaactctta      60
ggggtattat gtcattaact ttttaaaaat ctaccaatgt ggaaccagat tcagcaagaa     120
gaacaaggac aacatagatc cttacatata cacacccttt ggaagtggac ccagaaactg     180
cattggcatg aggtttgctc tcatgaacat gaaacttgct ctaatcagag tccttcagaa     240
cttctccttc aaaccttgta agaaacaca ggttagtcaa ttttctataa aaataatgtt      300
gtattaataa ttcttttaac tgagtggtct gtattttta aaaagaatat gcttgtttaa      360
tcttttacta atttgttctc tgggccaaag aatcaattag gcccatctgt g              411
```

<210> SEQ ID NO 163
<211> LENGTH: 288
<212> TYPE: DNA
<213> ORGANISM: Homo sapiens

<400> SEQUENCE: 163

```
ggagtgtctc actcactttg atgctatact ttctactttt gtttatttaa tgcttctcaa      60
tatgcttgtt taactgttgc agatccccct gaaattaagc ttaggaggac ttcttcaacc     120
agaaaaaccc gttgttctaa aggttgagtc aagggatggc actgtaagtg gagcctgaat     180
tttcctaagg acttctgctt tgctcttcaa gaaatctgtg cctgagaaca ccagagacct     240
caaattactt tgtgaataga actctgaaat gaagatgggc ttcatcca                  288
```

<210> SEQ ID NO 164
<211> LENGTH: 288
<212> TYPE: DNA
<213> ORGANISM: Homo sapiens

<400> SEQUENCE: 164

```
ggagtgtctc actcactttg atgctatact ttctactttt gtttatttaa tgcttctcaa      60
tatgcttgtt taactgttgc agatccccct gaaattaagc ttaggaggac ttcttcaacc     120
agaaaaaccc gttgttctaa aggttgagtc aagggatggc accgtaagtg gagcctgaat     180
tttcctaagg acttcggctt tgctcttcaa gaaatctgtg cctgagaaca ccagagacct     240
caaattactt tgtgaataga actctgaaat gaagatgggc ttcatcca                  288
```

<210> SEQ ID NO 165
<211> LENGTH: 236
<212> TYPE: DNA
<213> ORGANISM: Homo sapiens
<220> FEATURE:
<223> OTHER INFORMATION: r=g or a

<400> SEQUENCE: 165

```
ctacaaccat ggagacctcc acaactgatg taggacaaaa tgtttctgct ttgaactcta      60
gccttttggt ccagtgggat ttatgaaaag tgccatctct atagctgagg atgaagaatg     120
gaagagatta cratcattgc tgtctccaac cttccaccagt ggaaaactca aggaggtatg    180
aaaataacat gagttttaat aagaaactta agaatgaat ctggtgggga caggta          236
```

<210> SEQ ID NO 166
<211> LENGTH: 379
<212> TYPE: DNA
<213> ORGANISM: Homo sapiens
<220> FEATURE:
<223> OTHER INFORMATION: r=g or a, y=t or c, s=g or c, k=g or t

```
<400> SEQUENCE: 166 cccctttccaa ggggtagtcc actgaatttg agctgcctaa aaatggtctt ttatctttat      60
gtacagaaaa cacatcacaa aattcattat aaaatgtcac ttactgctcc atgctgggga     120
aagccatgtc cttctgggac tagagtctgc acatttaact atgggtggtg ttgtgttttg     180
tgcttagatg gtccctatca ttgcccagta tggagatgtg ttggtgagaa atctgaggcg     240
ggaagcagag acaggcaagc ctrtcacctt gaaasagtaa gtagaagcgc agcyatgggk     300
ttctgagctg tcatgaaccc ctccagckgc ctgccatgga gctgatattc ctgctgttgg     360
gttattccag tgaccagac                                                  379

<210> SEQ ID NO 167
<211> LENGTH: 431
<212> TYPE: DNA
<213> ORGANISM: Homo sapiens
<220> FEATURE:
<223> OTHER INFORMATION: r=g or a

<400> SEQUENCE: 167
cccagtgtac ctctgaattg cttttctatt cttttccctt agggatttga gggcttcact      60
tagatttctc ttcatctaaa ctgtgatgcc ctacattgat ctgatttacc taaaatgtct     120
ttcctctcct ttcagctctg tccgatctgg agctcgtggc ccaatcaatt atctttattt     180
ttgctggcta tgaaaccacg agcagtgttc tctccttcat tatgtatgaa ctggccactc     240
accctgatgt ccagcagaaa ctgcaggagg aaattgatgc agttttaccc aataaggtga     300
gtggatgrta catggagaag gagggaggag gtgaaaccct agcaaaaatg cctcctcacc     360
acttcccagg agaattttta taaaaagcat aatcactgat tctttcactg actctatgta     420
ggaaggctct g                                                          431

<210> SEQ ID NO 168
<211> LENGTH: 574
<212> TYPE: DNA
<213> ORGANISM: Homo sapiens
<220> FEATURE:
<223> OTHER INFORMATION: y=t or c, r=g or a

<400> SEQUENCE: 168
cagtatgagt tagtctctgg agctcctaat acttcattag tactgcatgg actgagttaa      60
aagttaattc aaaatctcaa tttatccaaa tctgtttcgt tctttccagg caccacccac     120
ctatgatact gtgctacaga tggagtatct tgacatggtg gtgaatgaaa yrctcagatt     180
attcccaatt gctatgagay ttgagagggt ctgcaaaaaa gatgttgaga tcaatgggat     240
gttcattccc aaaggggtgg tggtgatgat tccaagctat gctcttcacc gtgacccaaa     300
gtactggaca gagcctgaga agttcctccy tgaaaggtac aaggyccctg ggaagggagc     360
cctccctgaa ccagcctggt tcaagcatat tctgcctctc ttaatctaca ggacagtcat     420
gtggttgtat aattatttgc ttgtattttt atatttagag attttttttaa tcatcaaatt     480 gattattgtc acactttaca aaccatagac tagaaaaaag aaaactacag tcatccacaa     540
ttccaacaac ttacgatgaa ggtcatcagt tatg                                 574

<210> SEQ ID NO 169
<211> LENGTH: 411
<212> TYPE: DNA
<213> ORGANISM: Homo sapiens
<220> FEATURE:
<223> OTHER INFORMATION: y=t or c
```

```
<400> SEQUENCE: 169
cctgtgtact actagttgag gggtggcccc taagtaagaa accctaacat gtaactctta        60
ggggtattat gtcattaact ttttaaaaat ctaccaaygt ggaaccagat tcagcaagaa       120
gaacaaggac aacatagatc cttacatata cacacccttt ggaagtggac ccagaaactg       180
cattggcatg aggtttgctc tcatgaacat gaaacttgct ctaatcagag tccttcagaa       240
cttctccttc aaaccttgta aagaaacaca ggttagtcaa ttttctataa aaataatgtt       300
gtattaataa ttctttttaac tgagtggtct gtatttttta aaaagaatat gcttgtttaa      360
tcttttacta atttgttctc tgggccaaag aatcaattag gcccatctgt g                411

<210> SEQ ID NO 170
<211> LENGTH: 288
<212> TYPE: DNA
<213> ORGANISM: Homo sapiens
<220> FEATURE:
<223> OTHER INFORMATION: y=t or c, k=g or t

<400> SEQUENCE: 170
ggagtgtctc actcactttg atgctatact ttctactttt gtttatttaa tgcttctcaa        60
tatgcttgtt taactgttgc agatccccct gaaattaagc ttaggaggac ttcttcaacc       120
agaaaaaccc gttgttctaa aggttgagtc aagggatggc acygtaagtg gagcctgaat       180
tttcctaagg acttckgctt tgctcttcaa gaaatctgtg cctgagaaca ccagagacct       240
caaattactt tgtgaataga actctgaaat gaagatgggc ttcatcca                    288

<210> SEQ ID NO 171
<211> LENGTH: 30
<212> TYPE: DNA
<213> ORGANISM: Homo sapiens
<220> FEATURE:
<221> NAME/KEY: CDS
<222> LOCATION: (1)..(30)

<400> SEQUENCE: 171 cct gtc acc ttg aaa cac gtc ttt ggg gcc                                  30
Pro Val Thr Leu Lys His Val Phe Gly Ala
  1               5                  10

<210> SEQ ID NO 172
<211> LENGTH: 10
<212> TYPE: PRT
<213> ORGANISM: Homo sapiens

<400> SEQUENCE: 172

Pro Val Thr Leu Lys His Val Phe Gly Ala
  1               5                  10
```